(12) United States Patent
Pushpala et al.

(10) Patent No.: US 11,272,866 B2
(45) Date of Patent: Mar. 15, 2022

(54) WEARABLE MICRONEEDLE PATCH

(71) Applicant: One Drop Biosensor Technologies, LLC, New York, NY (US)

(72) Inventors: Ashwin Pushpala, San Francisco, CA (US); Matthew Chapman, San Francisco, CA (US); Alan Szmodis, San Francisco, CA (US); Abhijit Ghosh, San Francisco, CA (US)

(73) Assignee: One Drop Biosensor Technologies, LLC, New York, NY (US)

( * ) Notice: Subject to any disclaimer, the term of this patent is extended or adjusted under 35 U.S.C. 154(b) by 0 days.

(21) Appl. No.: 17/198,223

(22) Filed: Mar. 10, 2021

(65) Prior Publication Data

US 2021/0275097 A1    Sep. 9, 2021

Related U.S. Application Data

(63) Continuation of application No. 15/876,678, filed on Jan. 22, 2018, which is a continuation of application
(Continued)

(51) Int. Cl.
*A61B 5/145* (2006.01)
*A61B 5/1473* (2006.01)
(Continued)

(52) U.S. Cl.
CPC ........ *A61B 5/14514* (2013.01); *A61B 5/0002* (2013.01); *A61B 5/0004* (2013.01);
(Continued)

(58) Field of Classification Search
CPC ..... A61B 5/685; A61B 5/6833; A61B 5/1495; A61B 5/0022; A61B 5/0004; A61B 5/1473; A61B 5/14514
(Continued)

(56) References Cited

U.S. PATENT DOCUMENTS

| 4,953,552 A | 9/1990 | DeMarzo |
| 5,215,088 A | 6/1993 | Normann et al. |

(Continued)

FOREIGN PATENT DOCUMENTS

| CN | 1735375 | 2/2006 |
| CN | 102469941 | 5/2012 |

(Continued)

OTHER PUBLICATIONS

Adhikari, Basudam et al., "Polymers in sensor applications", Prog. Polym. Sci. vol. 29, pp. 699-766, Jan. 1, 2004.
(Continued)

*Primary Examiner* — Navin Natnithithadha
(74) *Attorney, Agent, or Firm* — Perkins Coie LLP

(57) ABSTRACT

A system and method for monitoring body chemistry of a user, the system comprising: a housing supporting: a microsensor comprising a first and second working electrode, a reference electrode, and a counter electrode, and configured to access interstitial fluid of the user, and an electronics subsystem comprising a signal conditioning module that receives a signal stream, from the microsensor, wherein the electronics subsystem is configured to detect an impedance signal derived from two of the first working electrode, the second working electrode, the reference electrode, and the counter electrode; and a processing subsystem comprising: a first module configured to generate an analysis indicative of an analyte parameter of the user and derived from the signal stream and the impedance signal, and a second module configured to transmit information derived from the analysis to the user, thereby facilitating monitoring of body chemistry of the user.

29 Claims, 21 Drawing Sheets

Related U.S. Application Data

No. 15/412,229, filed on Jan. 23, 2017, now abandoned, which is a continuation of application No. 15/377,318, filed on Dec. 13, 2016, now abandoned, which is a continuation of application No. 14/657,973, filed on Mar. 13, 2015, now abandoned.

(60) Provisional application No. 62/025,174, filed on Jul. 16, 2014, provisional application No. 62/012,874, filed on Jun. 16, 2014, provisional application No. 61/952,594, filed on Mar. 13, 2014.

(51) Int. Cl.
| | |
|---|---|
| *A61B 5/1495* | (2006.01) |
| *A61B 5/1486* | (2006.01) |
| *G16H 40/67* | (2018.01) |
| *H04W 12/037* | (2021.01) |
| *A61B 5/00* | (2006.01) |
| *A61B 5/11* | (2006.01) |
| *A61B 5/0537* | (2021.01) |
| *A61B 5/0538* | (2021.01) |
| *A61B 5/01* | (2006.01) |
| *A61B 17/34* | (2006.01) |

(52) U.S. Cl.
CPC .............. *A61B 5/0022* (2013.01); *A61B 5/01* (2013.01); *A61B 5/0537* (2013.01); *A61B 5/0538* (2013.01); *A61B 5/1118* (2013.01); *A61B 5/1451* (2013.01); *A61B 5/1473* (2013.01); *A61B 5/1495* (2013.01); *A61B 5/14532* (2013.01); *A61B 5/14546* (2013.01); *A61B 5/14865* (2013.01); *A61B 5/685* (2013.01); *A61B 5/688* (2013.01); *A61B 5/6833* (2013.01); *A61B 5/6849* (2013.01); *A61B 5/7275* (2013.01); *A61B 5/7278* (2013.01); *A61B 5/7285* (2013.01); *A61B 5/746* (2013.01); *A61B 17/3468* (2013.01); *G16H 40/67* (2018.01); *H04W 12/037* (2021.01); *A61B 5/6885* (2013.01); *A61B 2560/0223* (2013.01); *A61B 2562/028* (2013.01); *A61B 2562/0214* (2013.01); *A61B 2562/046* (2013.01); *A61B 2562/164* (2013.01)

(58) Field of Classification Search
USPC .......................................... 600/309, 345–366
See application file for complete search history.

(56) References Cited

U.S. PATENT DOCUMENTS

| | | | |
|---|---|---|---|
| 5,863,833 A | 1/1999 | Shin | |
| 5,949,739 A | 9/1999 | Reese | |
| 6,001,067 A | 12/1999 | Shults et al. | |
| 6,275,717 B1 | 8/2001 | Gross et al. | |
| 6,424,847 B1 | 7/2002 | Mastrototaro et al. | |
| 6,501,976 B1 | 12/2002 | Sohrab | |
| 6,560,471 B1 | 5/2003 | Heller et al. | |
| 6,582,573 B2 | 6/2003 | Douglas et al. | |
| 6,619,093 B2 | 9/2003 | Dawson et al. | |
| 6,690,959 B2 | 2/2004 | Thompson | |
| 6,699,667 B2 | 3/2004 | Keen | |
| 6,743,211 B1 | 6/2004 | Prausnitz et al. | |
| 6,749,792 B2 | 6/2004 | Olson | |
| 6,790,179 B2 | 9/2004 | Skover | |
| 6,793,632 B2 | 9/2004 | Sohrab | |
| 6,837,988 B2 | 1/2005 | Leong et al. | |
| 6,863,833 B1 | 3/2005 | Bloom et al. | |
| 6,875,613 B2 | 4/2005 | Shartle et al. | |
| 6,923,764 B2 | 8/2005 | Aceti et al. | |
| 7,029,444 B2 | 4/2006 | Shin et al. | |
| 7,295,867 B2 | 11/2007 | Berner et al. | |
| 7,322,960 B2 | 1/2008 | Yamamoto et al. | |
| 7,361,307 B2 | 4/2008 | Shartle et al. | |
| 7,399,585 B2 | 7/2008 | Gau | |
| 7,585,278 B2 | 9/2009 | Aceti et al. | |
| 7,591,801 B2 | 9/2009 | Brauker et al. | |
| 7,732,002 B2 | 6/2010 | Kodas et al. | |
| 7,753,888 B2 | 7/2010 | Mukerjee et al. | |
| 7,783,442 B2 | 8/2010 | Mueller et al. | |
| 7,885,697 B2 | 2/2011 | Brister et al. | |
| 7,920,906 B2 | 4/2011 | Goode et al. | |
| 7,946,984 B2 | 5/2011 | Brister et al. | |
| 7,949,382 B2 | 5/2011 | Jina | |
| 7,951,300 B2 | 5/2011 | Bhandari et al. | |
| 8,080,385 B2 | 12/2011 | Heller et al. | |
| 8,114,269 B2 | 2/2012 | Cooper et al. | |
| 8,224,414 B2 | 7/2012 | Kellogg et al. | |
| 8,280,475 B2 | 10/2012 | Brister et al. | |
| 8,280,476 B2 | 10/2012 | Jina | |
| 8,290,559 B2 | 10/2012 | Shariati et al. | |
| 8,361,037 B2 | 1/2013 | Gonnelli | |
| 8,386,027 B2 | 2/2013 | Chuang et al. | |
| 8,478,557 B2 | 7/2013 | Hayter et al. | |
| 8,565,849 B2 | 10/2013 | Kamath et al. | |
| 8,604,810 B2 | 12/2013 | Sheppard | |
| 8,608,924 B2 | 12/2013 | Cooper et al. | |
| 8,615,282 B2 | 12/2013 | Brister et al. | |
| 8,641,672 B2 | 2/2014 | Yodfat et al. | |
| 8,663,106 B2 | 3/2014 | Stivoric et al. | |
| 8,668,645 B2 | 3/2014 | Drucker et al. | |
| 8,677,188 B2 | 3/2014 | Eickmeyer et al. | |
| 8,700,114 B2 | 4/2014 | Gottlieb et al. | |
| 8,718,742 B2 | 5/2014 | Beck et al. | |
| 8,734,348 B2 | 5/2014 | Say et al. | |
| 8,744,545 B2 | 6/2014 | Say et al. | |
| 8,744,547 B2 | 6/2014 | Budiman et al. | |
| 8,774,887 B2 | 7/2014 | Say et al. | |
| 8,792,953 B2 | 7/2014 | Brister et al. | |
| 8,808,532 B2 | 8/2014 | Yang et al. | |
| 8,858,912 B2 | 10/2014 | Boyden et al. | |
| 8,865,288 B2 | 10/2014 | Bhandari et al. | |
| 8,882,670 B2 | 11/2014 | Hancock | |
| 8,886,279 B2 | 11/2014 | Tathireddy et al. | |
| 8,965,477 B2 | 2/2015 | Hoss et al. | |
| 9,008,745 B2 * | 4/2015 | Pushpala .......... | A61B 5/150022 600/345 |
| 9,011,332 B2 | 4/2015 | Heller et al. | |
| 9,044,199 B2 | 6/2015 | Brister et al. | |
| 9,055,901 B2 | 6/2015 | Brister et al. | |
| 9,182,368 B2 * | 11/2015 | Pushpala .............. | A61B 5/1495 |
| 9,192,328 B2 | 11/2015 | Brauker et al. | |
| 9,195,799 B2 | 11/2015 | Sze et al. | |
| 9,215,995 B2 | 12/2015 | Gottlieb et al. | |
| 9,220,483 B2 | 12/2015 | Frankhouser et al. | |
| 9,278,174 B2 | 3/2016 | Gray | |
| 9,357,951 B2 | 6/2016 | Simpson et al. | |
| 9,387,000 B2 | 7/2016 | Corrie et al. | |
| 9,402,544 B2 | 8/2016 | Yee et al. | |
| 9,414,777 B2 | 8/2016 | Brister et al. | |
| 9,474,478 B2 | 10/2016 | Bhavaraju et al. | |
| 9,498,159 B2 | 11/2016 | Heller et al. | |
| 9,504,411 B2 | 11/2016 | Engelhardt et al. | |
| 9,532,741 B2 | 1/2017 | Brauker et al. | |
| 9,603,557 B2 | 3/2017 | Brister et al. | |
| 9,615,851 B2 | 4/2017 | Neinast et al. | |
| 9,632,060 B2 | 4/2017 | Shah et al. | |
| 9,662,047 B2 | 5/2017 | Barman et al. | |
| 9,737,247 B2 | 8/2017 | Wang et al. | |
| 9,743,870 B2 | 8/2017 | Wang et al. | |
| 9,814,389 B2 | 11/2017 | DeHennis | |
| 9,974,471 B1 | 5/2018 | Kam et al. | |
| 10,046,114 B1 | 8/2018 | Biederman et al. | |
| 10,070,820 B2 | 9/2018 | Huang | |
| 10,098,574 B1 * | 10/2018 | Kam ................... | A61B 5/1455 |
| 10,136,846 B2 | 11/2018 | Wang et al. | |
| 10,173,042 B2 * | 1/2019 | Pushpala ............ | A61B 5/14865 |
| 10,238,289 B2 | 3/2019 | Hagi | |
| 10,321,858 B2 | 6/2019 | Maiz-Aguinaga et al. | |
| 10,327,678 B2 | 6/2019 | Gottlieb et al. | |

(56) References Cited

U.S. PATENT DOCUMENTS

| | | | |
|---|---|---|---|
| 10,383,558 B2 | 8/2019 | Cho et al. | |
| 10,524,730 B2 | 1/2020 | Reitz et al. | |
| 10,549,080 B2 * | 2/2020 | Pushpala | A61B 5/14532 |
| 10,595,754 B2 | 3/2020 | Pushpala et al. | |
| 10,667,733 B2 | 6/2020 | Simpson et al. | |
| 10,765,369 B2 | 9/2020 | Antonio et al. | |
| 10,799,158 B2 | 10/2020 | Brister et al. | |
| 10,799,159 B2 | 10/2020 | Brister et al. | |
| 10,806,384 B2 | 10/2020 | Frey et al. | |
| 10,813,577 B2 | 10/2020 | Brister et al. | |
| 10,820,860 B2 * | 11/2020 | Pushpala | A61B 5/150984 |
| 10,827,954 B2 | 11/2020 | Hoss et al. | |
| 10,835,161 B2 | 11/2020 | Simpson et al. | |
| 10,863,932 B1 * | 12/2020 | Kam | A61B 5/1455 |
| 10,874,335 B2 | 12/2020 | Cho et al. | |
| 11,172,851 B2 | 11/2021 | Pushpala et al. | |
| 2002/0015963 A1 | 2/2002 | Keen | |
| 2002/0028991 A1 * | 3/2002 | Thompson | A61B 5/685 |
| | | | 600/372 |
| 2002/0062202 A1 | 5/2002 | Arai | |
| 2002/0123048 A1 | 9/2002 | Gau | |
| 2003/0100821 A1 | 5/2003 | Heller et al. | |
| 2003/0130616 A1 | 7/2003 | Steil et al. | |
| 2004/0049219 A1 | 4/2004 | Briggs et al. | |
| 2004/0060902 A1 | 4/2004 | Evans et al. | |
| 2004/0260241 A1 | 12/2004 | Yamamoto et al. | |
| 2005/0004438 A1 | 1/2005 | Ward et al. | |
| 2005/0245839 A1 | 11/2005 | Stivoric et al. | |
| 2006/0015058 A1 | 1/2006 | Kellogg et al. | |
| 2006/0016700 A1 | 1/2006 | Brister et al. | |
| 2006/0258929 A1 | 11/2006 | Goode et al. | |
| 2006/0264716 A1 | 11/2006 | Zander | |
| 2007/0004989 A1 * | 1/2007 | Dhillon | A61B 5/14514 |
| | | | 600/583 |
| 2007/0032717 A1 | 2/2007 | Brister et al. | |
| 2007/0179371 A1 | 8/2007 | Peyser et al. | |
| 2007/0208245 A1 | 9/2007 | Brauker et al. | |
| 2007/0219480 A1 | 9/2007 | Kamen et al. | |
| 2008/0033254 A1 | 2/2008 | Kamath et al. | |
| 2008/0058726 A1 | 3/2008 | Jina et al. | |
| 2008/0114280 A1 | 5/2008 | Stafford | |
| 2008/0138582 A1 | 6/2008 | Bhandari et al. | |
| 2008/0154107 A1 | 6/2008 | Jina | |
| 2008/0319285 A1 | 12/2008 | Hancock | |
| 2009/0036794 A1 | 2/2009 | Stubhaug et al. | |
| 2009/0156924 A1 | 6/2009 | Shariati et al. | |
| 2009/0294307 A1 | 12/2009 | Liu et al. | |
| 2009/0301994 A1 | 12/2009 | Bhandari et al. | |
| 2009/0321277 A1 | 12/2009 | Heller et al. | |
| 2010/0010601 A1 | 1/2010 | Negi et al. | |
| 2010/0016687 A1 | 1/2010 | Brauker et al. | |
| 2010/0030045 A1 | 2/2010 | Gottlieb et al. | |
| 2010/0075353 A1 | 3/2010 | Heaton | |
| 2010/0112195 A1 | 5/2010 | Kodas et al. | |
| 2010/0113897 A1 | 5/2010 | Brenneman et al. | |
| 2010/0152651 A1 | 6/2010 | Boyden et al. | |
| 2010/0298895 A1 | 11/2010 | Ghaffari et al. | |
| 2010/0324392 A1 | 12/2010 | Yee et al. | |
| 2011/0009824 A1 | 1/2011 | Yodfat et al. | |
| 2011/0029269 A1 | 2/2011 | Hayter et al. | |
| 2011/0053121 A1 | 3/2011 | Heaton | |
| 2011/0060202 A1 * | 3/2011 | Miller | A61B 5/14514 |
| | | | 600/345 |
| 2011/0089957 A1 | 4/2011 | Sheppard | |
| 2011/0125058 A1 | 5/2011 | Levinson et al. | |
| 2011/0237917 A1 | 9/2011 | Roy et al. | |
| 2011/0257456 A1 | 10/2011 | Kinn et al. | |
| 2011/0257495 A1 | 10/2011 | Hoss et al. | |
| 2011/0319734 A1 | 12/2011 | Gottlieb et al. | |
| 2012/0035442 A1 | 2/2012 | Barman et al. | |
| 2012/0046533 A1 | 2/2012 | Voskanyan et al. | |
| 2012/0078071 A1 | 3/2012 | Bohm et al. | |
| 2012/0108931 A1 | 5/2012 | Taub et al. | |
| 2012/0165639 A1 | 6/2012 | Engelhardt et al. | |
| 2012/0190950 A1 | 7/2012 | Yang et al. | |
| 2012/0190952 A1 | 7/2012 | Stafford | |
| 2012/0203078 A1 | 8/2012 | Sze et al. | |
| 2012/0209244 A1 | 8/2012 | Gray | |
| 2012/0209303 A1 | 8/2012 | Frankhouser et al. | |
| 2012/0215087 A1 | 8/2012 | Cobelli et al. | |
| 2012/0238841 A1 | 9/2012 | Castle et al. | |
| 2012/0265042 A1 | 10/2012 | Neinast et al. | |
| 2013/0150691 A1 | 6/2013 | Pace | |
| 2013/0178726 A1 | 7/2013 | Wang et al. | |
| 2013/0190583 A1 | 7/2013 | Grosman et al. | |
| 2013/0225956 A1 | 8/2013 | Huang et al. | |
| 2013/0245401 A1 | 9/2013 | Estes et al. | |
| 2013/0248364 A1 | 9/2013 | Kahn et al. | |
| 2013/0267811 A1 | 10/2013 | Pryor et al. | |
| 2013/0310665 A1 | 11/2013 | Crean et al. | |
| 2013/0328578 A1 | 12/2013 | Shah et al. | |
| 2013/0331676 A1 | 12/2013 | Morgan et al. | |
| 2013/0338598 A1 | 12/2013 | Gyrn | |
| 2014/0012117 A1 * | 1/2014 | Mensinger | A61B 5/742 |
| | | | 600/365 |
| 2014/0012118 A1 * | 1/2014 | Mensinger | A61B 5/6898 |
| | | | 600/365 |
| 2014/0012510 A1 | 1/2014 | Mensinger et al. | |
| 2014/0039275 A1 * | 2/2014 | Chang | A61B 5/0022 |
| | | | 600/301 |
| 2014/0066735 A1 | 3/2014 | Engelhardt et al. | |
| 2014/0088392 A1 * | 3/2014 | Bernstein | A61B 5/743 |
| | | | 600/365 |
| 2014/0088393 A1 * | 3/2014 | Bernstein | G16H 50/20 |
| | | | 600/365 |
| 2014/0259652 A1 * | 9/2014 | Pushpala | A61B 5/14503 |
| | | | 29/825 |
| 2014/0275897 A1 | 9/2014 | Pushpala et al. | |
| 2015/0038897 A1 | 2/2015 | Daddona et al. | |
| 2015/0182725 A1 | 7/2015 | Finger et al. | |
| 2015/0257685 A1 * | 9/2015 | Pushpala | A61B 5/1118 |
| | | | 600/345 |
| 2015/0257687 A1 * | 9/2015 | Pushpala | A61B 5/1118 |
| | | | 600/345 |
| 2016/0022187 A1 * | 1/2016 | Pushpala | A61B 5/150022 |
| | | | 600/347 |
| 2016/0038180 A1 | 2/2016 | Kube et al. | |
| 2017/0086713 A1 * | 3/2017 | Pushpala | A61B 5/7278 |
| 2017/0086724 A1 * | 3/2017 | Pushpala | A61B 5/14514 |
| 2017/0095652 A1 * | 4/2017 | Pushpala | A61B 5/150984 |
| 2017/0127984 A1 * | 5/2017 | Pushpala | A61B 5/14865 |
| 2017/0128009 A1 * | 5/2017 | Pushpala | A61B 5/150969 |
| 2017/0172475 A1 | 6/2017 | Pushpala et al. | |
| 2017/0188912 A1 | 7/2017 | Halac et al. | |
| 2017/0251958 A1 * | 9/2017 | Pushpala | A61B 5/685 |
| 2018/0140235 A1 | 5/2018 | Pushpala et al. | |
| 2018/0177439 A1 * | 6/2018 | Sia | A61B 5/150984 |
| 2018/0368771 A1 | 12/2018 | Gray et al. | |
| 2019/0104976 A1 | 4/2019 | Reynolds et al. | |
| 2019/0150806 A1 * | 5/2019 | Mou | A61B 5/157 |
| 2020/0101286 A1 * | 4/2020 | Windmiller | A61B 5/05 |
| 2020/0121902 A1 * | 4/2020 | Pushpala | A61B 5/150427 |
| 2020/0178853 A1 | 6/2020 | Pushpala et al. | |
| 2020/0390395 A1 * | 12/2020 | Pushpala | A61B 5/14514 |
| 2020/0405234 A1 * | 12/2020 | Pushpala | A61B 5/14865 |
| 2021/0100504 A1 * | 4/2021 | Pushpala | A61B 5/150427 |
| 2021/0100505 A1 * | 4/2021 | Pushpala | A61B 5/14503 |
| 2021/0204845 A1 | 7/2021 | Pushpala et al. | |
| 2021/0236057 A1 | 8/2021 | Pushpala et al. | |

FOREIGN PATENT DOCUMENTS

| | | |
|---|---|---|
| CN | 103458810 | 12/2013 |
| EP | 1266608 | 8/2006 |
| EP | 2327362 | 6/2011 |
| JP | 4112499 | 7/2008 |
| JP | 4373604 | 11/2009 |
| JP | 4439733 | 3/2010 |
| JP | 4574847 | 11/2010 |
| JP | 4905906 | 3/2012 |
| JP | 5021115 | 9/2012 |

(56) References Cited

FOREIGN PATENT DOCUMENTS

| | | |
|---|---|---|
| JP | 2013502978 | 1/2013 |
| JP | 5591715 | 9/2014 |
| JP | 5640110 | 12/2014 |
| JP | 2015505251 | 2/2015 |
| JP | 5680960 | 3/2015 |
| JP | 5749751 | 7/2015 |
| JP | 5795584 | 10/2015 |
| JP | 2016508763 | 3/2016 |
| JP | 2016517601 | 6/2016 |
| JP | 2016518881 | 6/2016 |
| WO | 1994020602 | 9/1994 |
| WO | 1999045387 | 9/1999 |
| WO | 2000074763 | 12/2000 |
| WO | 2002062202 | 8/2002 |
| WO | 2002097414 | 12/2002 |
| WO | 2008028087 | 3/2008 |
| WO | 2008157820 | 12/2008 |
| WO | 2009082699 | 7/2009 |
| WO | 2009105145 | 8/2009 |
| WO | 2011025549 | 3/2011 |
| WO | 2013058879 | 4/2013 |
| WO | 2013163035 | 10/2013 |
| WO | 2014145001 | 9/2014 |
| WO | 2014145049 | 9/2014 |
| WO | 2015002940 | 1/2015 |

OTHER PUBLICATIONS

Chinese Office Action application No. 2014800271779, dated Feb. 2, 2017.
Chinese Office Action application No. 2015800127310, dated Jul. 24, 2018.
European Office Action application No. 14770855.6, dated Nov. 25, 2016.
European Office Action application No. 15762313.3, dated Sep. 29, 2017.
European Office Action application No. 15762313.3, dated Mar. 20, 2019.
International Search Report and Written Opinion for International Patent Application No. PCT/US2014/027655. dated Sep. 5, 2014. 10 pages.
International Search Report and Written Opinion for International Patent Application No. PCT/US2015/020586. dated Jun. 24, 2015. 9 pages.
U.S. Appl. No. 15/876,678, filed Jan. 22, 2018, System for Monitoring Body Chemistry.
U.S. Appl. No. 17/156,520, filed Jan. 22, 2021, Wearable Microneedle Patch System for Monitoring Body Chemistry.
U.S. Pat. No. 10/595,595, Mar. 24, 2020, System for Monitoring Body Chemistry.
U.S. Appl. No. 16/791,518, filed Feb. 14, 2020, System for Monitoring Body Chemistry.
U.S. Appl. No. 17/182,097, Feb. 22, 2021, System for Monitoring Body Chemistry.

* cited by examiner position 84b downward force places outward biasing force on triggers, 86

Shown in configuration 188a. Downward force on 88 releases trigger (188) to accelerate plunger (84') downward in configuration 188b

200

S210 — receiving a second housing portion into an opening of a first housing portion, the first housing portion supporting a microsensor including a first working electrode, a second working electrode, a reference electrode, and a counter electrode, and the second housing portion supporting an electronics subsystem configured to receive a signal stream from the microsensor S220 — after interfacing with the second housing portion, accelerating the second housing portion toward skin of the user thereby delivering sensing regions of the microsensor into interstitial fluid of the user S230 — generating an impedance signal, from two of the first working electrode, the second working electrode, the reference electrode, and the counter electrode, in response to applying a voltage, near a shifted potential different than a reference potential of the reference electrode S240 — at a processing system in communication with the electronics subsystem, receiving the signal stream and the impedance signal S250 — at the processing system, generating an analysis indicative of an analyte parameter of the user and derived from the signal stream and the impedance signal S260 — transmitting information derived from the analysis to an electronic device associated with the user, thereby facilitating monitoring of body chemistry of the user

FIGURE 20

WEARABLE MICRONEEDLE PATCH

CROSS-REFERENCE TO RELATED APPLICATION(S)

This application is a continuation of U.S. application Ser. No. 15/876,678, filed Jan. 22, 2018, which is a continuation of U.S. application Ser. No. 15/412,229, filed Jan. 23, 2017, which is a continuation of U.S. application Ser. No. 15/377,318, filed Dec. 13, 2016, which is a continuation of U.S. application Ser. No. 14/657,973, filed Mar. 13, 2015, which claims priority to U.S. Provisional Application No. 62/025,174, filed Jul. 16, 2014, U.S. Provisional Application No. 62/012,874, filed Jun. 16, 2014, and U.S. Provisional Application No. 61/952,594, filed Mar. 13, 2014, all of which are incorporated by reference herein in their entireties.

TECHNICAL FIELD

This invention relates generally to the biometric device field, and more specifically to a new and useful system for monitoring body chemistry in the biometric device field.

BACKGROUND

Biomonitoring devices are commonly used, particularly by health-conscious individuals and individuals diagnosed with ailments, to monitor body chemistry. Such biomonitoring devices perform the tasks of determining an analyte level in a user's body, and providing information regarding the analyte level to a user; however, these current biomonitoring devices typically convey information to users that is limited in detail, intermittent, and prompted by the command of the user. Such biomonitoring devices, including blood glucose meters, are also inappropriate for many applications outside of intermittent use, and place significant burdens on users (e.g., in requiring finger sticks, in requiring lancing, etc.) due to design and manufacture considerations. Additionally, current devices are configured to analyze one or a limited number of analytes contributing to overall body chemistry, due to limitations of sensors used in current biomonitoring devices.

There is thus a need in the biometric device field to create a new and useful system for monitoring body chemistry. This invention provides such a new and useful system.

BRIEF DESCRIPTION OF THE FIGURES

FIG. 20 depicts an embodiment of a method for monitoring body chemistry.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. System

Figure 1:
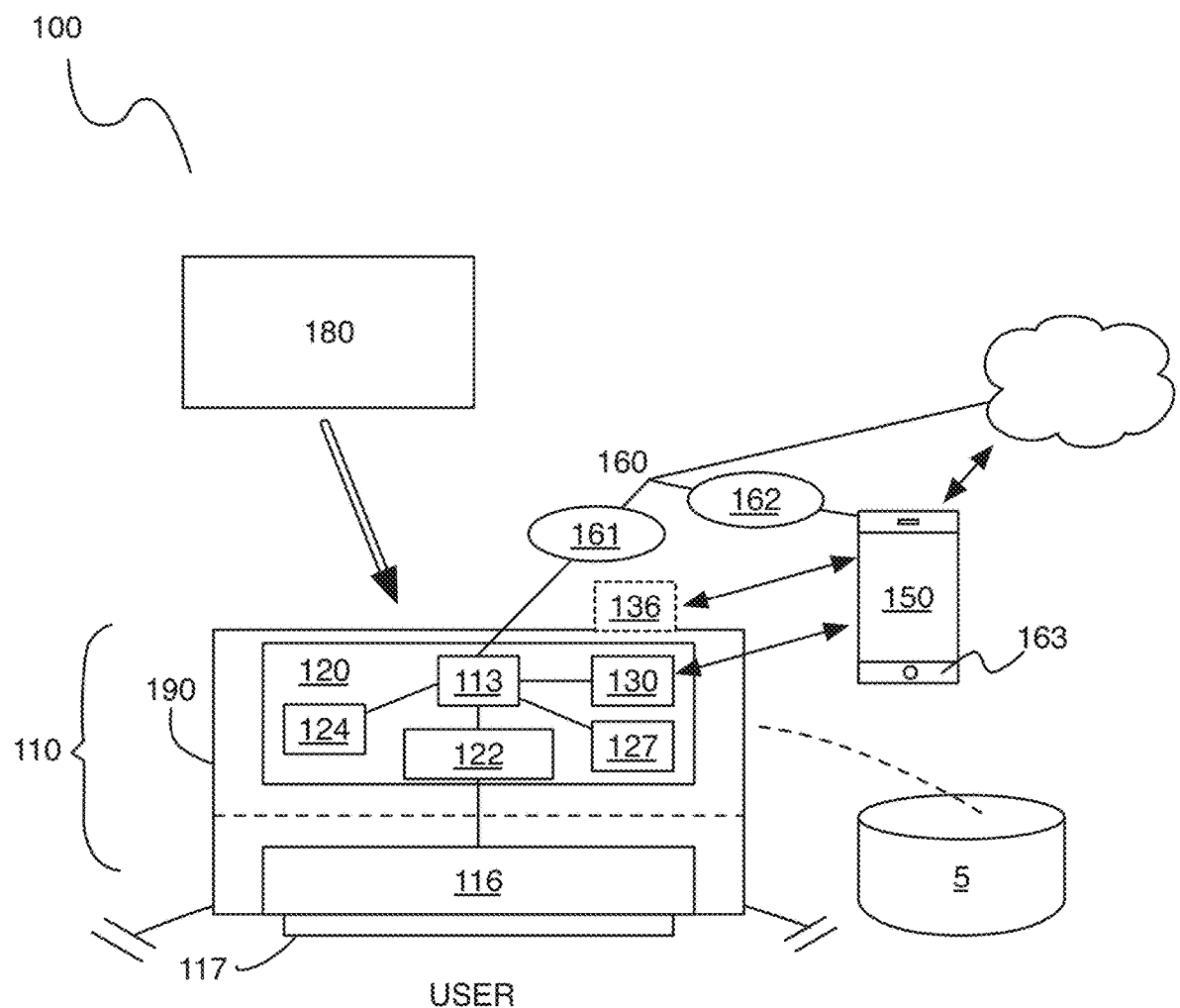
FIG. 1 depicts elements of an embodiment of a system for monitoring body chemistry.

As shown in FIG. 1, an embodiment of the system 100 for monitoring body chemistry of a user comprises a housing 190 that supports a microsensor 116 and an electronics subsystem 120 in communication with the microsensor 116; and a processing subsystem 160 configured to generate an analysis indicative of an analyte parameter of the user, wherein the analysis is derived from a signal stream of the microsensor and an impedance signal from the electronics subsystem. In more detail, the housing 190, microsensor 116, and the electronics subsystem 120 can be configured as a microsensor patch 110 configured to sense analyte levels in a user's body, wherein the electronics subsystem includes a signal conditioning module 122, a power management module 124, a storage module 127, and a transmitting unit 130 in communication with the processing subsystem 160 and/or an electronic device (e.g., mobile computing device 150) associated with the user.

In some variations, the system 100 can further include a patch applicator 180 configured to facilitate application of the microsensor patch 110 onto the body of a user in a reliable manner. The system 100 functions to provide continuous monitoring of a user's body chemistry through reception and processing of signals associated with one or more analytes present in the body of the user, and to provide an analysis of the user's body chemistry to the user and/or an entity (e.g., health care professional, caretaker, relative, friend, acquaintance, etc.) associated with the user. Alternatively, the system 100 can function to detect a user's body chemistry upon the user's request or sporadically, and/or can provide an analysis of the user's body chemistry only to the user.

The system 100 is configured to be worn by the patient outside of a clinical (e.g., hospital) or research (e.g., laboratory) setting, such that the patient can be in a non-contrived environment as he or she is interfacing with the microsensor patch 110 for monitoring of body chemistry. Furthermore, elements of the system 100 can be reusable or disposable (e.g., based upon modularity of the system 100), or the entire system 100 can be configured to be disposable. In one specific example, the system 100 adheres to the patient (thus not compelling the patient to hold any part of the system 100 by hand), has a low profile that conforms to the patient, and is configured to receive and transmit signals indicative of body chemistry parameters of the user, for downstream analysis and information transfer to the user. Alternatively, the system 100 can be substantially non-portable, non-wearable, and/or intended for use in a clinical or research setting.

As indicated above and further below, elements of the system can be implemented on one or more computer networks, computer systems, or applications servers, etc. The computer system(s) can comprise one or more of: a cloud-based computer, a mainframe computer system, a grid-computer system, or any other suitable computer system, and the computer system can support collection of data from a wearable device and/or a base station, processing of these data, and transmission of alerts, notifications, and/or user interface updates to one or more electronic computing devices (e.g., mobile computing device, wrist-borne mobile computing device, head-mounted mobile computing device, etc.) linked to or affiliated with an account of the user. For example, the computer system can receive signals indicative of one or more analyte parameters of the user and distribute alerts and notifications over a distributed network, such as over a cellular network or over an Internet connection. In this example, the computer system can upload alerts and notifications to a native body chemistry monitoring application including the user interface and executing on a mobile computing device associated with the user.

Additionally or alternatively, an electronic computing device (e.g., a laptop computer, a desktop computer, a tablet, a smartphone, a smart watch, a smart eyewear accessory, a personal data assistant, etc.) associated with the system (e.g., with the account of the user) can maintain the account of the user, create and maintain a user-specific model within the account, and execute a native body chemistry monitoring application (including the user interface) with functions including one or more of: generating alerts or notifications, receiving alerts or notifications, displaying alerts or notifications, updating predictions of changes in state of the user, and any other suitable function that enhances body chemistry monitoring of the user. The system 100 is preferably configured to implement at least a portion of the method 200 described in Section 2 below; however, the system 100 can additionally or alternatively be configured to implement any other suitable method.

1.1 System—Microsensor Patch

As shown in FIG. 1, the microsensor patch 110 comprises a microsensor 116 and an electronics subsystem 120 in communication with the microsensor 116, wherein the microsensor 116 and the electronics subsystem 120 are supported by a housing 190. The microsensor patch 110 can be configured to detect and sense only a single analyte; however, the microsensor patch 110 can alternatively be configured to detect and sense multiple analytes in order to provide an analysis based on multiple analytes. Preferably, the microsensor patch 110 is configured to be disposable; however, the microsensor patch 110 can alternatively be configured to be reusable for any suitable duration or number of uses. In one variation, the microsensor patch 110 is configured to be a semi-permanent component (e.g., wearable for a week before replacement, wearable for a month before replacement, etc.) configured to sense the user's body chemistry with minimal signal degradation for at a least a week post-coupling of the microsensor patch 110 to the body of the user. However, in another variation, the microsensor patch 110 can be configured to be a permanent component configured to permanently couple to a user. Modularity of the microsensor patch 110 is described in further detail below.

1.1.1 System—Microsensor

Figure 2A:
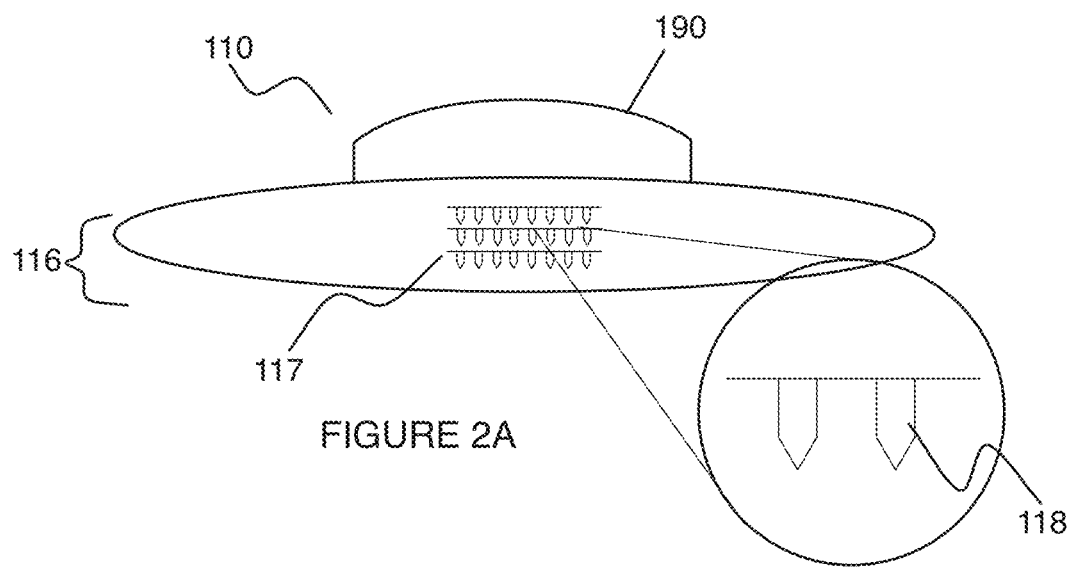
FIGS. 2A and 2B depict embodiments of a microsensor patch, a transmitting unit, a housing, and an array of filaments in an embodiment of a system for monitoring body chemistry.

The microsensor 116 of the microsensor patch 110 preferably comprises an array of filaments 117, as shown in FIGS. 1 and 2A, and functions to penetrate skin of the user in order to sense one or more analytes characterizing the user's body chemistry. Preferably, the array of filaments 117 is configured to penetrate the user's stratum corneum (i.e., an outer skin layer) in order to sense analytes within interstitial (extracellular) fluid, which is throughout the body; however, the array of filaments 117 can be configured to penetrate the user's skin to any other suitable depth. For instance, the microsensor 116 can alternatively be configured to penetrate deeper layers, or various depth layers of a user's skin in order to sense analytes within any appropriate bodily fluid of the user. The microsensor 116 can be configured to sense analytes/ions characterizing a user's body chemistry using a potentiometric measurement (e.g., for small analytes including potassium, sodium calcium, etc.), using an amperometric measurement (e.g., for large analytes including glucose, lactic acid, creatinine, etc.), using a conductometric measurement, and/or using any other suitable measurement.

Preferably, sensed analytes result in a signal (e.g., voltage, current, resistance, capacitance, impedance, gravimetric, etc.) detectable by the electronics subsystem 120 in communication with the microsensor 116; however, analyte sensing can comprise any other appropriate mechanism using the microsensor 116. As mentioned earlier, the microsensor 116 is also preferably integrated with the electronics subsystem 120. In a first variation, the microsensor 116 is coupled to the semiconductor architecture of the electronics subsystem 120 (e.g., the microsensor 116 is coupled to an integrated circuit comprising the electronics subsystem 120), in a second variation, the microsensor 116 is more closely integrated into the semiconductor architecture of the electronics subsystem 120 (e.g., there is closer integration between the microsensor 116 and an integrated circuit including the electronics subsystem 120), and in a third variation, the microsensor 116 and the electronics subsystem 120 are constructed in a system-on-a-chip fashion (e.g., all components are integrated into a single chip). As such, in some variations, filaments the array of filaments 117 of the microsensor 116 can be directly or indirectly integrated with electronics components, such that preprocessing of a signal from the microsensor 116 can be performed using the electronics components (e.g., of the array of filaments 117, of the electronics subsystem 120) prior to or after transmitting signals to the electronics subsystem 120 (e.g., to an analog front end, to an analog to digital converter). The electronics components can be coupled to a filament substrate, or otherwise integrated with the filaments in any suitable fashion (e.g., wired, using a contact pad, etc.). Alternatively, the electronics components can be fully integrated into the electronics subsystem 120 and configured to communicate with the microsensor 116, or the electronics components can be split between the microsensor and the electronics subsystem 120. The microsensor 116 can, however, comprise any other suitable architecture or configuration.

The microsensor 116 preferably senses analyte parameters using the array of filaments 117, such that absolute values of specific analytes/ions can be detected and analyzed. The microsensor 116 can additionally be configured to sense analyte parameters using the array of filaments 117, such that changes in values of specific analyte/ion parameters or derivatives thereof (e.g., trends in values of a parameter, slopes of curves characterizing a trend in a parameter vs. another parameter, areas under curves characterizing a trend, a duration of time spent within a certain parameter range, etc.) can be detected and analyzed. In one variation, sensing by the microsensor 116 is achieved at a low frequency at discrete time points (e.g., every minute, or every hour), and in another variation, sensing by the microsensor 116 is achieved substantially continuously at a high frequency (e.g., every picosecond, every millisecond, every second). In one specific example for blood chemistry analysis, the array of filaments 117 of the microsensor 116 is configured to sense one or more of: electrolytes, glucose, bicarbonate, creatinine, body urea nitrogen (BUN), sodium, iodide, iodine and potassium of a user's blood chemistry. In another specific example, the array of filaments 117 of the microsensor 116 is configured to sense at least one of biomarkers, cell count, hormone levels, alcohol content, gases (e.g. carbon dioxide, oxygen, etc.), drug concentrations/metabolism, pH and analytes within a user's body fluid.

As shown in FIG. 2A, the array of filaments 117 is preferably located at the base surface of the microsensor patch 110, and functions to interface directly with a user in a transdermal manner (e.g., in accessing interstitial fluid) in order to sense at least one analyte/ion characterizing the user's body chemistry. The array of filaments 117 is preferably arranged in a uniform pattern with a specified density optimized to effectively penetrate a user's skin and provide an appropriate signal, while minimizing pain to the user. Additionally, the array of filaments 117 can be arranged in a manner to optimize coupling to the user, such that the microsensor firmly couples to the user over the lifetime usage of the system. For example, the filaments 118 can comprise several pieces and/or be attached to a flexible base to allow the array of filaments 117 to conform to a user's body. In one variation, the array of filaments 117 is arranged in a rectangular pattern, and in another variation, the array of filaments 117 is arranged in a circular or ellipsoid pattern. However, in other variations, the array of filaments 117 can be arranged in any other suitable manner (e.g., a random arrangement). The array of filaments 117 can also be configured to facilitate coupling to a user, by comprising filaments 118 of different lengths or geometries. Having filaments 118 of different lengths can further function to allow measurement of different ions/analytes at different depths of penetration (e.g., a filament with a first length can sense one analyte at a first depth, and a filament with a second length can sense another analyte at a second depth). The array of filaments 117 can also comprise filaments 118 of different geometries (e.g., height, diameter) to facilitate sensing of analytes/ions at lower or higher concentrations. In one specific example, the array of filaments 117 is arranged at a density of 100 filaments per square centimeter and each filament 118 in the array of filaments 117 has a length of 250-350 microns, which allows appropriate levels of detection, coupling to a user, and pain experienced by the user.

Figure 2B:
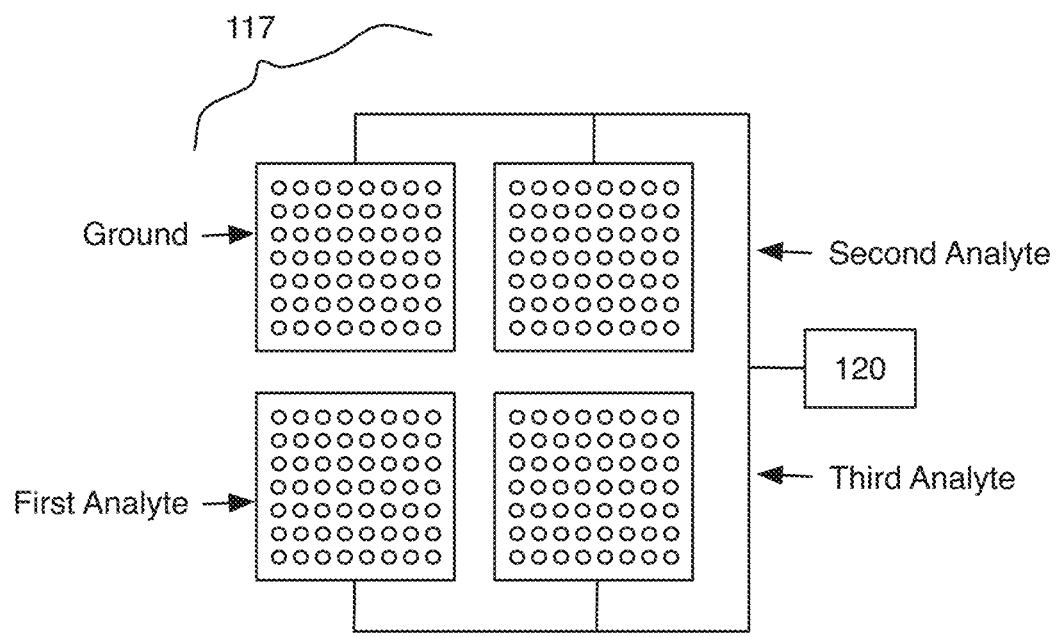
Figure 2C:
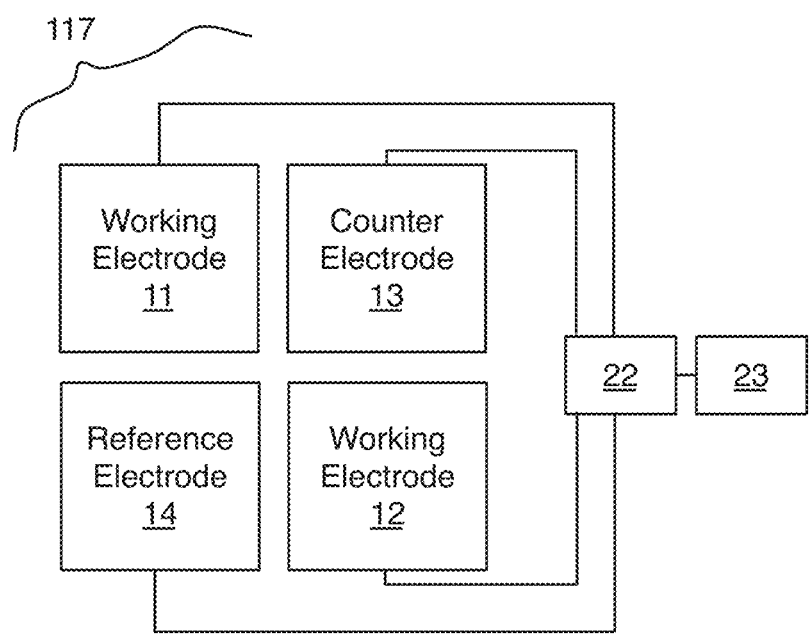
FIG. 2C depict a variation of electrodes in an embodiment of a system for monitoring body chemistry.
Figure 3A:
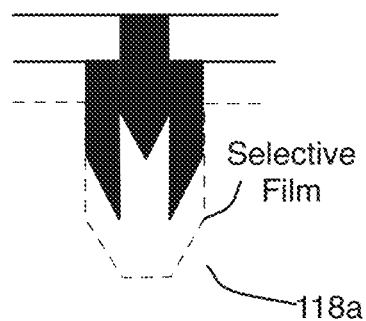
FIGS. 3A-3H depict examples of filament variations in an embodiment of a system for monitoring body chemistry.
Figure 3B:
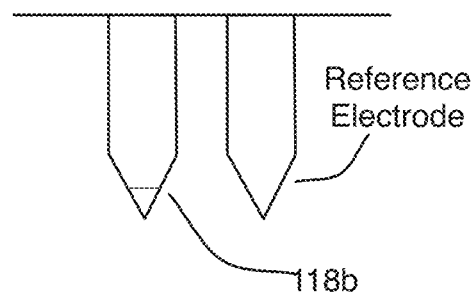
Figure 3C:
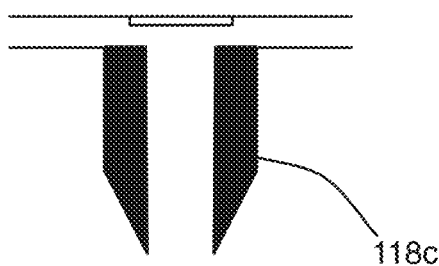
Figure 3D:
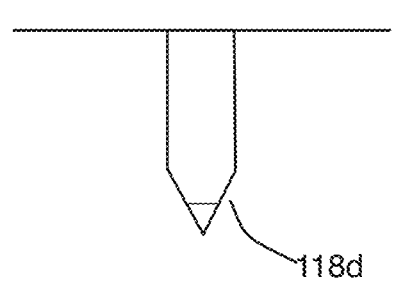
Figure 3E:
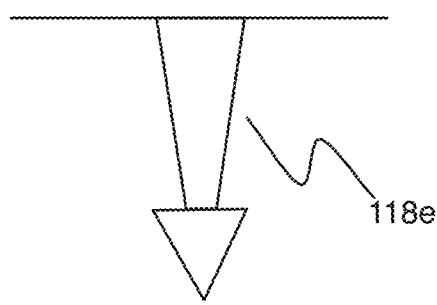
Figure 3F:
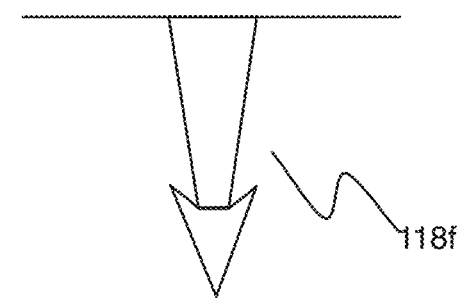
Figure 3G:
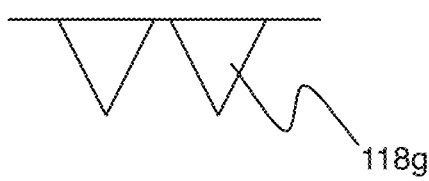
Figure 3H:
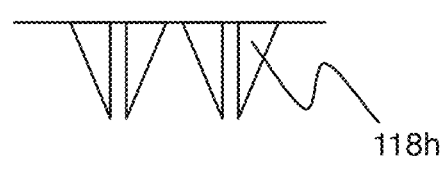

Each filament 118 in the array of filaments 117 preferably functions to sense a single analyte; however, each filament 118 in the array of filaments 117 can additionally be configured to sense more than one analyte. Furthermore, the array of filaments 117 can be further configured, such that a subarray of the array of filaments 117 functions as a single sensor configured to sense a particular analyte or biomarker, as shown in FIG. 2B. Furthermore, any configuration of subarrays of the array of filaments 117 can additionally or alternatively be configured as one or more of: a working electrode, a counter electrode (i.e., auxiliary electrode), and a reference electrode, for instance, in a two-electrode cell, a three-electrode cell, or a more-than-three-electrode cell. In one variation, as shown in FIG. 2C, the array of filaments 117 of the microsensor 116 is configured as a first working electrode 11 (corresponding to a first subarray of filaments), a second working electrode 12 (corresponding to a second subarray of filaments), a counter electrode 13 (corresponding to a third subarray of filaments), and a reference electrode 14 (corresponding to a fourth subarray of filaments). In a specific example of this variation, each subarray associated with the first working electrode 11, the second working electrode 12, the counter electrode 13, and the reference electrode 14, respectively, is substantially identical in morphology (e.g., area of the microsensor). Furthermore, in the specific example, each subarray has a square footprint, and the subarrays are configured in a 2×2 arrangement to define a larger square footprint. However, the array of filaments 117 can be configured as one or more of: a working electrode, a counter electrode, and a reference electrode in any other suitable manner, and can furthermore have any other suitable morphology(ies) and/or configuration relative to each other.

Additionally or alternatively, any subarray of the array of filaments 117 can be configured to release biomaterials (e.g., therapeutic substances, drugs) for treating a medical condition of a user (e.g., as facilitated by biomaterial dissolution in interstitial fluid). Multiple subarrays of the array of filaments can then be configured to sense different analytes/biomarkers, or the same analyte/biomarker. Furthermore, a subarray or a single filament 118 of the array of filaments 117 can be configured as a ground region of the microsensor 116, such that signals generated by the microsensor 116 in response to analyte detection can be normalized by the signals generated by the subarray or single filament 118 serving as a ground region. Preferably, all subarrays of the array of filaments 117 are substantially equal in size and density; however, each subarray of the array of filaments 117 can alternatively be optimized to maximize signal generation and detection in response to a specific analyte. In an example, analytes that are known to have a lower concentration within a user's body fluid can correspond to a larger subarray of the array of filaments 117. In another example, analytes that are known to have a higher concentration within a user's body fluid can correspond to a smaller subarray of the array of filaments 117. In one extreme example, an entire array of filaments can be configured to sense a single analyte, such that the microsensor 116 and microsensor patch 110 is configured to sense and detect only one analyte. In another extreme example, each single filament in an array can be configured to detect a single analyte allowing for detection of multiple analytes within a single array (e.g., for a 100-filament array, 100 analytes can be tested).

In other variations, a subarray of the array of filaments 117 can also be used to detect other physiologically relevant parameters, such as electrophysiological signals (e.g., electrocardiogram, electroencephalogram), body temperature, respiration, and skin impedance change (e.g., to measure hydration state or inflammatory response). In these other variations, the subarray can be dedicated to measuring these physiologically relevant parameters, which could be combined with analyte/ion parameter measurements in order to provide meaningful information to a user. As an example, the simultaneous measurement of potassium levels and electrocardiogram measurements, enabled by subarrays of the array of filaments 117, can provide a more complete diagnosis of cardiovascular problems or events than either measurement by itself.

A filament 118 of the array of filaments can comprise one or more of: a substrate core, the substrate core including a base end coupled to the substrate, a columnar protrusion having a proximal portion coupled to the base end and a distal portion, and a tip region coupled to the distal portion of the columnar protrusion and that facilitates access to the body fluid of the user; a conductive layer, isolated to the tip region of the substrate core and isolated away from the base end and the columnar protrusion as an active region that enables transmission of electronic signals generated upon detection of an analyte; an insulating layer ensheathing the columnar protrusion and base end of the substrate core and exposing a portion of the conductive layer, thereby defining a boundary of the active region; a sensing layer, in communication with the active region, characterized by reversible redox behavior for transduction of an ionic concentration of the analyte into an electronic signal; an intermediate selective layer superficial to the conductive layer and deeper than the sensing layer, relative to a most distal point of the tip region of the filament, that facilitates detection of the analyte; an intermediate protective layer, superficial to the intermediate selective layer, including a functional compound that promotes generation of a protective barrier; and a selective coating superficial to the intermediate protective layer, having a distribution of molecules that respond to presence of the analyte, superficial to the sensing layer. Thus, a filament can comprise one or more regions, morphologies (examples of which are shown in FIGS. 3A-3H, with elements 118a-118h), compositions, and/or configurations as described in U.S. Pub. No. 2014/0275897, entitled "On-Body Microsensor for Biomonitoring" and filed on 14 Mar. 2014 and/or U.S. App. No. 62/025,174, and entitled "System for Monitoring Body Chemistry" and filed on 16 Jul. 2014, which are each incorporated herein in their entirety by this reference. However, the filament can additionally or alternatively comprise any other suitable region, composition, morphology, and/or configuration.

1.1.2 System—Electronics Subsystem

Figure 4:
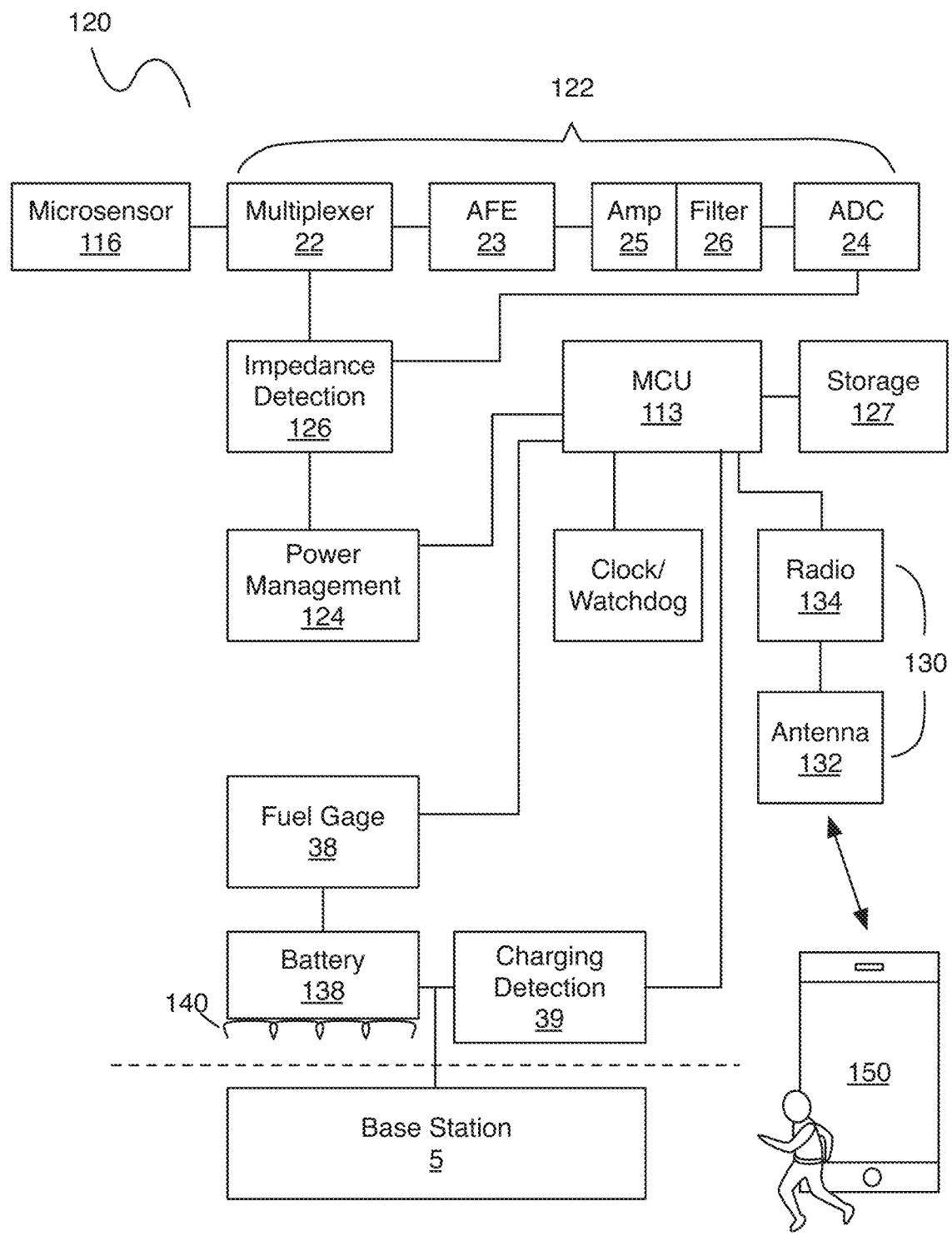
FIG. 4 depicts an embodiment of an electronics subsystem in an embodiment of a system for monitoring body chemistry.

The electronics subsystem 120 functions to receive analog signals from the microsensor 116 and to convert them into digital signals to be processed by a microprocessor 113 of the electronics subsystem 120. In receiving signals, processing signals, regulating function, storing data, and/or transmitting data, the electronics subsystem 120 preferably includes a microprocessor 113 interfacing with one or more of: a signal conditioning module 122, a power management module 124, an impedance detection module 126, a storage module 127, and a transmitting unit 130, as shown in FIG. 4. However, the electronics subsystem 120 can additionally or alternatively include any other suitable modules configured to facilitate signal reception, signal processing, and data transfer in an efficient manner.

The microprocessor 113 preferably includes memory and/or is coupled to a storage module 127 (e.g., flash storage). The microprocessor 113 can also include and/or be coupled to a clock/watchdog module (which can be incorporated into a microcontroller unit) for control of timing between different functions of the electronics subsystem 120. The microprocessor 113 functions to process received signals, enable power distribution, enable impedance monitoring, and enable data transmission from the electronics subsystem 120, in relation to other portions of the electronics subsystem 120 described below; however, the microprocessor 113 can alternatively or additionally be configured to perform any other suitable function.

The signal conditioning module 122 functions to preprocess signals detected and received using the microsensor 116, thereby producing conditioned data prior to processing at the processing subsystem 160. The signal conditioning module 122 can include one or more of: a signal multiplexer, an analog front end, an amplifier (e.g., a variable gain amplifier), a filter (e.g., low pass filter, high pass filter, band pass filter, etc.), an analog-to-digital converter (ADC), and a digital-to-analog converter (DAC). In one variation, as shown in FIG. 4, the signal conditioning module 122 comprises a multiplexer 22 in communication with the microsensor 116, wherein the multiplexer 22 is configured to communicate an output to an analog front end 23 that interfaces the microsensor 116 with an ADC 24 by way of a variable gain amplifier 25 coupled to a filter 26. In a specific example of this variation, the analog front end 23 circuitry is configured with a shifted potential different than a reference potential of the reference electrode 14 of the microsensor 116, wherein the shifted potential is different (e.g., −2V to 2V different) from the reference potential of the reference electrode 14. The configuration involving a difference between the shifted potential and the reference potential can allow the system 100 to drive redox reactions at the surface of the microsensor 110. However, in alternative variations of the specific example, the analog front end (or any other element of the signal conditioning module 122) can be configured with any other suitable potential relative to potentials of electrodes of the microsensor 116.

In more detail, the multiplexer 22 of the signal conditioning module 122 is preferably configured to receive multiple signals from the microsensor 116 (e.g., from subarrays of the array of filaments 117) and to forward the multiple signals received at multiple input lines in a single line at the analog front end. The multiplexer 22 thus increases an amount of data that can be transmitted within a given time constraint and/or bandwidth constraint. The number of input channels to the multiplexer 22 is preferably greater than or equal to the number of output channels of the microsensor 116, and can have any suitable relationship between the number of input lines into the multiplexer 22, select lines of the multiplexer, and output lines from the multiplexer 22. In some variations, the multiplexer 22 can include a post-multiplexer gain in order to reduce capacitance values of the analog front end 23 coupled to the multiplexer 22, and which can also be used to limit a number of amplifiers of the electronics 120, such that a single amplifier is coupled to the multiplexer 22 (as opposed to amplifiers coupled to each individual sensor); however, the multiplexer 22 can alternatively not include any gain producing elements. In some variations, the multiplexer 22 can additionally or alternatively include high frequency and/or low frequency limiting elements. However, the multiplexer 22 can additionally or alternatively be configured in any other suitable manner. Furthermore, in alternative variations, the signal conditioning module 122 can omit a multiplexer and/or comprise or omit any other suitable element.

Figure 5A:
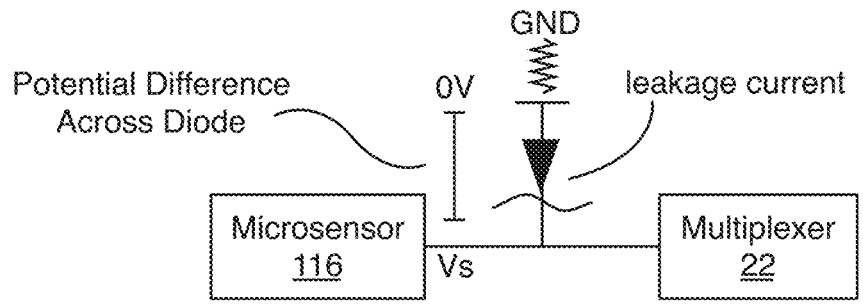
FIGS. 5A-5C depict examples of a portion of an electronics subsystem in an embodiment of a system for monitoring body chemistry.
Figure 5B:
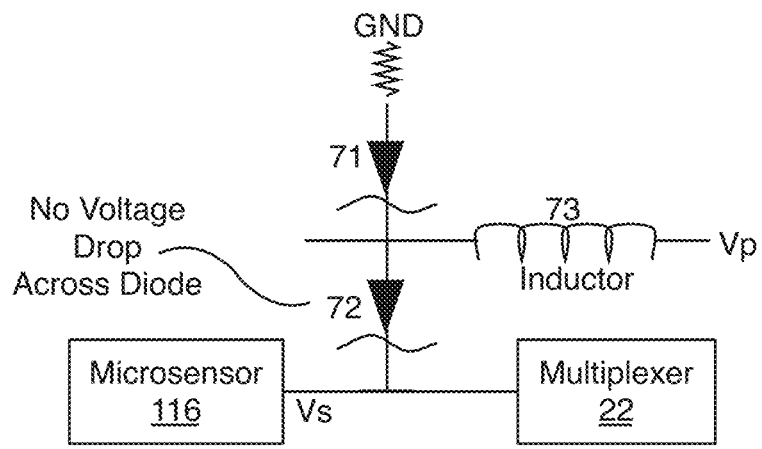
Figure 5C:
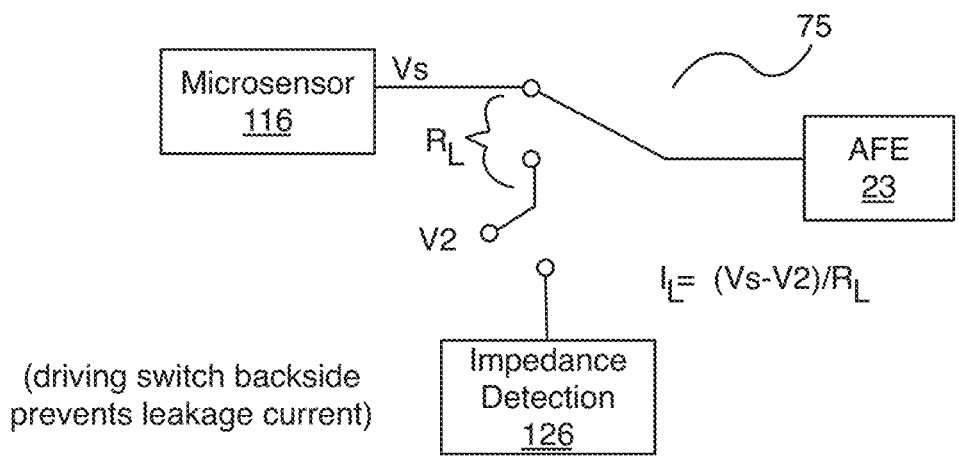

In variations, an interface between the microsensor 116 and other elements of the electronics subsystem 120 can be configured in a manner that prevents or otherwise reduces leakage current effects due to a redox potential of the microsensor 16 in relation to other elements electronics subsystem 120. In a first configuration, a leakage current effect can result when a diode to ground (e.g., an ESD-diode to ground) is configured at an interface between the microsensor 116 and a multiplexer 22, as shown in FIG. 5A. To prevent or otherwise reduce the leakage current effect, a set of diodes 70, comprising a first diode 71 (e.g., a first EST-diode) and a second diode 72 (e.g., a second ESD-diode), configured at an interface between the microsensor 116 and the multiplexer 22 can be coupled to an element 73 (e.g., inductor, ferrite bead, resistor, etc.) that provides a high resistance to transient voltage spikes and directs any discharge through the second diode 72 to ground (instead of damaging the electronics subsystem 120), as shown in FIG. 5B. The multiplexer 22 can also comprise a switch 75, as shown in FIG. 5C, that allows altering of potentials within the analog front end 23. As shown in FIG. 5C, eliminating a voltage difference (i.e., between Vs and $V_2$) eliminates or otherwise reduces leakage currents that can affect readings from the microsensor 110.

The power management module 124 functions to provide dynamic modulation of power transfer to and from elements of the microsensor patch 110, in a manner that enables efficient operation of the system 100. Preferably, the power management module 124 interfaces with a battery 138 and elements of the transmitting unit 130 requiring power (e.g., by way of a microprocessor 113, as shown in FIG. 4), as described in further detail below. Additionally, the power management module 124 can further interface with an external processing element of the processing subsystem 160, such that the power management module 124 can be at least partially implemented in firmware. In one such variation of the power management module 124, wherein power management is achieved in firmware, the power management module 124 can be configured to anticipate power requirements of one or more elements, and to automatically operate at the highest demanded power mode (e.g., voltage) required, while never dropping below a minimum power level required by the elements. The power management module 124 can also facilitate efficient switching of components to an "off" state when not needed, in order to contribute to lower current consumption. Additionally or alternatively, the power management module 124 can be configured to dynamically trigger high current draw sensing components (e.g., the impedance detection module 126) to an "on" state, only when needed, by monitoring other system components (e.g., voltage of a counter electrode 13).

Figure 6A:
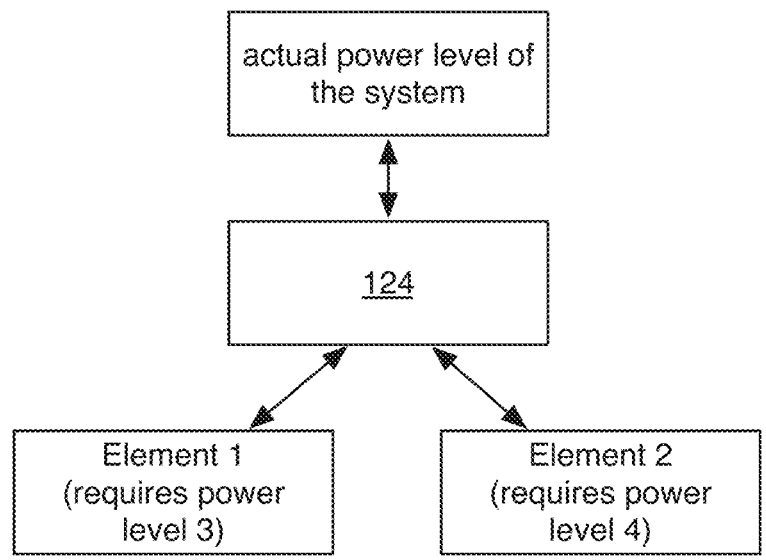
FIGS. 6A-6B depict examples of power management modules in an embodiment of a system for monitoring body chemistry.

In an example, as shown in FIG. 6A, a group of elements requiring different operating power levels can be coupled to the power management module 124, and the power management module 124 can output power at the highest operating power level anticipated among the elements. Disparate elements can also set a minimum level of power they require, and as elements vary their power requirements, the power management module 124 can then automatically adjust power output such that a power level provided never drops below the lowest power level required. In this variation, elements of the microsensor patch no requiring power are thus dynamically provided with their highest demanded power level, to substantially limit energy wasted by the system 100 and to satisfy power level requirements of all running elements. In another variation of the power management module 124, wherein power management is achieved in firmware, the power management module 124 can be configured to detect elements requiring power, and to automatically operate at the highest demanded power mode (e.g., voltage) required. In an example, a group of elements requiring different operating voltages can be detected, and the power management module 124 can output power at the highest operating voltage detected. As elements vary their voltage requirements, the power management module 124 can then automatically adjust voltage output to meet the highest demanded voltage. In this variation, elements of the microsensor patch 110 requiring power are thus dynamically provided with their highest demanded voltage, to substantially limit energy wasted by the system 100.

Figure 6B:
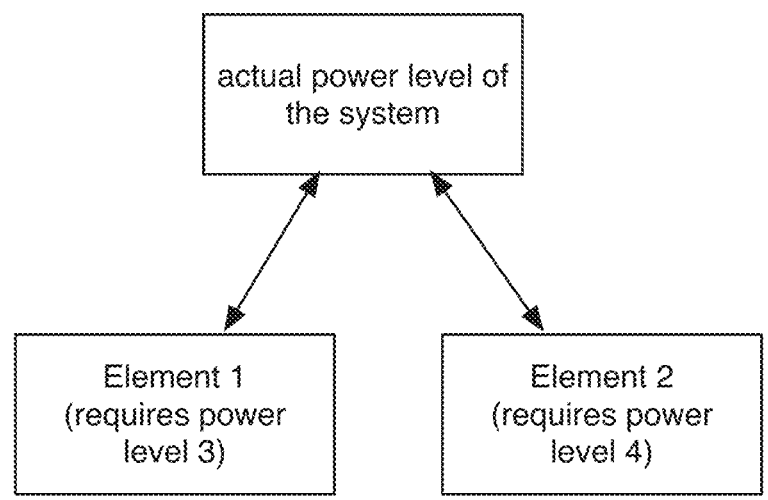

In other variations, power management can be achieved by the power management module 124 without implementation in firmware, such that power management occurs in circuitry. In these other variations, an example of which is shown in FIG. 6B, power management can comprise providing a set amount of power to elements requiring power, and completely eliminating power transfer to elements not requiring power. The system 100 can, however, comprise any other suitable variation of the power management modules 124.

In relation to the power management module 124, the electronics subsystem 120 can comprise a battery 138, which functions to serve as a power source for the electronics subsystem 120. The battery 138 is preferably coupled to a fuel gage 38 and a charging detection module 39, each of which is coupled to the microprocessor 113 (described in further detail below). The battery 138 is preferably a lithium-ion battery that is configured to be rechargeable, but can be any appropriate rechargeable battery (e.g., nickel-cadmium, nickel metal hydride, or lithium-ion polymer). Alternatively, the battery 138 may not be a rechargeable battery. Preferably, the battery 138 is configured to have a profile with a low aspect ratio, contributing to a thin form factor of the microsensor patch 110. However, the battery 138 can be configured to have any appropriate profile such that the battery 130 provides adequate power characteristics (e.g., cycle life, charging time, discharge time, etc.) for the system 100. In some variations, a thin-film battery can be integrated with the microsensor patch no in order to facilitate substantially continuous analyte detection by the system 100, independent of the microprocessor 113 and digital electronics of the electronics subsystem 120.

In embodiments where the battery 138 is rechargeable, the electronics subsystem 120 can also comprise a charging coil 140 that functions to provide inductive charging for the battery 138, and a charging detection module 39, in communication with the microprocessor 113, that enable detection of charging of the battery 138. The charging coil 140 is preferably coupled to the battery 138 and converts energy from an electromagnetic field (e.g., provided by an element of a base station, as described in further detail below), into electrical energy to charge the battery 138. Inductive charging provided by the charging coil 140 thus facilitates user mobility while interacting with the system 100. In alternative variations, however, the charging coil 140 can altogether be omitted (e.g., in embodiments without a rechargeable battery), or replaced by a connection configured to provide wired charging of a rechargeable battery.

Additionally or alternatively, in some variations, the microsensor patch 110 can comprise a semi-active or fully-active power cell (e.g., implementing microelectromechanical system elements) that functions to absorb and/or release generated energy from any one or more of: body heat of the user, body movement of the user (e.g., with piezoelectric elements, with capacitive elements), static voltage from the environment of the user, light in the environment of the user (e.g., using solar cells), magnetic energy flux, galvanic differentials, and any other suitable energy source to provide secondary backup energy for the system 100.

The impedance detection module 126 is in communication with the signal conditioning module 122 and the power management module 124, and functions to enable detection of a proper interface between the microsensor 116 and body fluid (e.g., interstitial fluid) of the user. In facilitating monitoring of impedance, the impedance detection module 126 can thus provide signals that indicate that the microsensor patch 110 is properly coupled to the user (e.g., interfacing with interstitial fluid and experiencing an ~80% moisture environment) or improperly coupled to the user (e.g., not interfacing properly with interstitial fluid and experiencing a low-moisture environment). Signals from the impedance detection module 126 can further be used to trigger an error correction action (e.g., notification for the user to reapply the microsensor patch 110, automatic manipulation of the microsensor patch 110 to re-establish interface with body fluid, etc.). In one variation, as shown in FIG. 4, the impedance detection module can comprise electronic circuitry configured to communicate with the multiplexer 22, the ADC 24, and the power management module 124, in receiving an impedance signal from the microsensor 116. However, the impedance detection module 126 can additionally or alternatively be configured relative to other elements of the electronics subsystem 120 in any other suitable manner.

Figure 7:
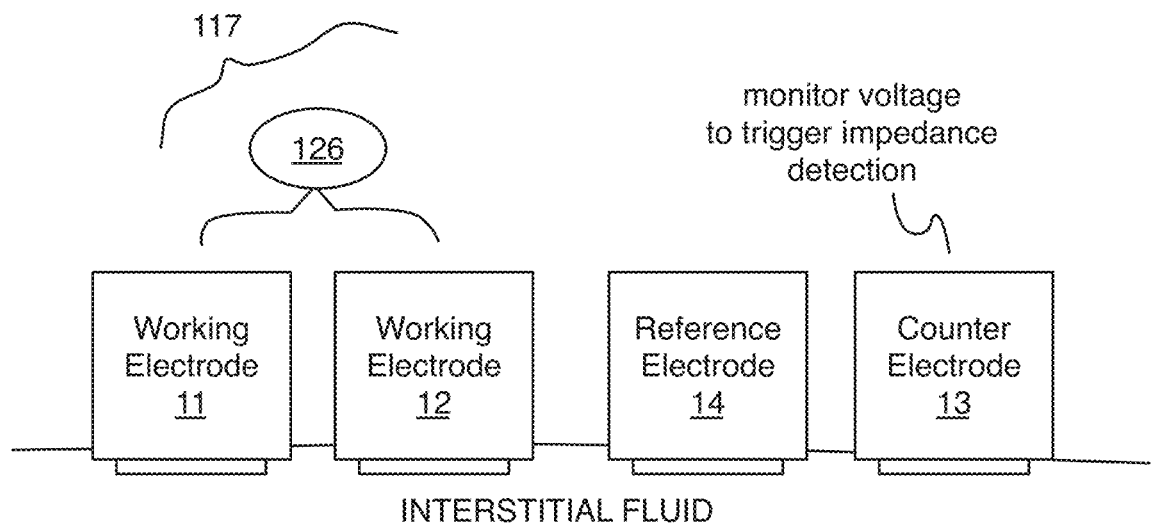
FIG. 7 depicts a variation of an impedance detection module in an embodiment of a system for monitoring body chemistry.

In generating the impedance signal, the impedance detection module 126 can be configured to detect impedance between two electrodes of the array of filaments 117 in response to an applied voltage provided in cooperation with the power management module 126 and the microprocessor 113. In one variation, wherein the microsensor 116 comprises a first working electrode 11, a second working electrode 12, a counter electrode 13, and a reference electrode, the impedance detection module 126 can be configured to detect impedance from two of the first working electrode 11, the second working electrode 12, the counter electrode 13, and the reference electrode 14, examples of which are shown in FIG. 7. In a specific example, an applied signal can be injected into the system in a working electrode and detected in the reference electrode 14. However in other configurations of the microsensor 116, the impedance detection module 126 can be configured to detect impedance from electrodes of the microsensor 116 in any other suitable manner.

Figure 8:
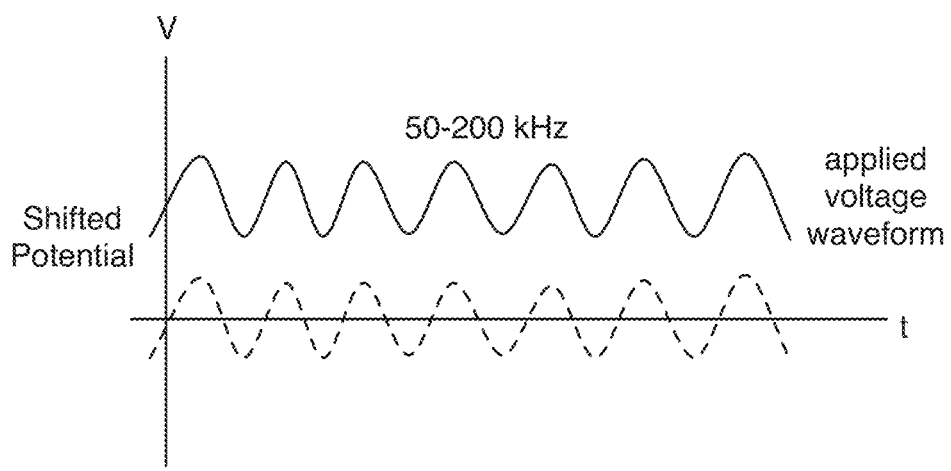
FIG. 8 depicts an example of an applied voltage waveform in an embodiment of a system for monitoring body chemistry.

In relation to the applied voltage used for generation and reception of the impedance signal (i.e., for purposes of perturbation), the electronics subsystem 120 is preferably configured to provide an applied voltage waveform having a characteristic value (e.g., average value) near the operating potential of the signal conditioning module 122 of the electronics subsystem 120. In a variation wherein the signal conditioning module 122 (e.g., an analog front end 23 of the signal conditioning module 122) operates at a shifted potential relative to a potential of an electrode of the microsensor 116 (e.g., a reference potential of a reference electrode), the applied voltage waveform preferably has a characteristic value (e.g., average value) near or equal to that of the shifted potential, in order to improve stability of the microsensor no when switching back to a current sensing mode (i.e., the primary detection mode). The offset (i.e., shifted potential) is configured to reduce or minimize any disruption to signal integrity when the microsensor no is switched from a current sensing mode to an impedance detection mode, and then back to a current sensing mode. In a specific example, as shown in FIG. 8, the applied voltage waveform is shifted about a characteristic value and has a frequency from 50-200 kHz, in relation to a shifted potential of the analog front end 23 relative to the reference electrode 14. However, the applied voltage can alternatively have any other suitable characteristics (e.g., characteristic voltage values, frequencies, etc.) defined in relation to the operating potential(s) of any other suitable element of the electronic subsystem 120 related to the microsensor 116.

In relation to triggering of a measurement using the impedance detection module 126, triggering can occur with any suitable frequency (e.g., in relation to the lifespan of usage of the system 100), any suitable regularity (e.g., at regular time intervals, at irregular time intervals, etc.), and/or upon any suitable triggering event. In one variation, the impedance detection module 126 can be configured to provide an impedance signal in association with monitoring of an electrode (e.g., monitoring voltage of the counter electrode 13) of the microsensor 116, wherein detection of an out-of-range parameter (e.g., voltage) of the electrode triggers the applied voltage waveform and generation of an impedance signal. As such, the electronics subsystem 120 and the processing subsystem 160 (described further below) can be configured to cooperate in continuously detecting a voltage parameter of the counter electrode 13, and the electronics subsystem 120 can be configured to apply the applied voltage waveform and detect the impedance signal when the voltage parameter of the counter electrode satisfies a voltage threshold condition.

Additionally or alternatively, in another variation, the impedance detection module 126 can be configured to provide an impedance signal upon initial application of the system 100 to the body of the user. Additionally or alternatively, in another variation, the impedance detection module 126 can be configured to provide impedance signals at regular time intervals (e.g., once every hour) over the course of use of the system 100 by the user. Additionally or alternatively, in relation to other sensors (e.g., of a mobile computing device associated with the user and the system 100, of a wearable computing device associated with the user and the system 100, of the system 100, etc.) the impedance detection module 126 can be configured to provide an impedance signal in response to a sensor signal that indicates performance of an action by the user. For instance, monitoring of signals provided by an accelerometer and/or gyroscope can be used to indicate that the user is exercising, and that an impedance measurement should be taken (e.g., during exercise, after exercise, etc.) to ensure proper coupling of the system 100 to the user. In another example, monitoring of body temperature of the user can be used to indicate that the user is showering, and that an impedance measurement should be to ensure proper coupling of the system 100 to the user. The impedance detection module 126 can, however, be configured in any other suitable manner.

The impedance detection module 126 can further be used to generate notifications pertaining to impedance signal measurements that indicate improper coupling. For instance, a notification can be generated (and transmitted to a mobile computing device of the user) in response to detection of unsuitable impedance derived from comparison between the impedance signal and an impedance threshold condition. However, use of the impedance signal in performing an error correction action can be performed in any other suitable manner.

The transmitting unit 130 functions to receive signals generated by the microsensor patch 110 (e.g., by way of the microprocessor 113), and to interface with at least one of a mobile computing device 150, a data processing and/or storage module (e.g., a module external to an on-board storage module, a cloud-based computing module, etc.) by outputting signals based on at least one analyte parameter. The transmitting unit 130 thus cooperates with other elements of the electronics subsystem 120 to transmit signals based on sensed analyte parameters, which can be used to facilitate analyses of the user's body chemistry. In variations, the transmitting unit 130 includes an antenna 132, a radio 134 coupling the antenna to the microprocessor 113, and can additionally or alternatively include a linking interface 136 (e.g., wireless or wired interface, as described in further detail below).

Preferably, the transmitting unit 130 and the microsensor patch 110 are integrated as a cohesive unit; however, the transmitting unit 130 and the microsensor patch no can alternatively form a modular unit, wherein one of the transmitting unit 130 and the microsensor patch 110 is disposable, and wherein one of the transmitting unit 130 and the microsensor patch no is reusable. In variations of the microsensor patch no and the transmitting unit 130, elements of the microsensor patch no aside from the microsensor 116 can alternatively be integrated with the transmitting unit 130, such that the transmitting unit 130 is configured to be reusable and the microsensor 116 of the microsensor patch 110 is configured to be disposable. Modularity in the system 100 is described in further detail in relation to the housing 190 below.

Additionally, the transmitting unit 130 is preferably configured to output signals based on at least one analyte parameter characterizing body chemistry continuously over the lifetime usage of the transmitting unit 130; however, the transmitting unit 130 can alternatively be configured to output signals based on at least one analyte parameter at a set of time points (e.g., minutes, hours, days). Still alternatively, the transmitting unit 130 can be configured to output signals in a manner that does not interfere with other operations (e.g., signal collection operations) of the electronics subsystem 120. In one such example, the transmitting unit 130 can be configured to stop signal transmission whenever the ADC 24 is collecting signal data from the microsensor 116, in coordination with timing enabled by a clock/watchdog module associated with the microprocessor 113. In variations, the transmitting unit 130 can be further configured to output signals upon a user prompt, and/or can comprise a variable sampling rate. For example, the sampling an be lower when user is asleep, higher during activity (e.g., exercise), higher when there is a sudden change in a value, higher in response to other stimuli (e.g., if glucose spikes, sampling rate increases for all analytes).

The antenna 132 of the transmitting unit 130 functions to convert electrical signals from the microsensor patch no into radio waves, to facilitate communication with one or more devices external to the microsensor patch no and/or transmitting unit 130 assembly (e.g., by a Bluetooth Low Energy connection). The antenna 132 preferably interfaces with a radio 134 coupled to the microprocessor 113, as shown in FIG. 4, but can additionally or alternatively interface with other elements of the transmitting unit 130. The antenna is preferably an omnidirectional antenna that radiates radio wave power uniformly primarily in one plane, with the power decreasing with elevation angle relative to the plane; however, the antenna can alternatively be an isotropic antenna that has a spherical radiation patent. Other variations of the antenna can include any appropriate antenna that can be integrated with the form factor of the transmitting unit, while providing appropriate communication with external devices.

The radio 134 functions to transmit and receive signals from the antenna 132, and also facilitates communication with elements of the transmitting unit 130 and external devices. The radio 134 and the antenna 132 can additionally or alternatively be supplemented with a linking interface 136, as described in further detail below, but can additionally or alternatively interface with other elements of the electronics subsystem 120.

The linking interface 136 functions to transmit an output of at least one element of the microsensor patch no/transmitting unit 130 assembly to a mobile computing device 150. Additionally, the linking interface 136 can function to transmit and output of at least one element of the microsensor patch no and transmitting unit 130 assembly to another element external to the microsensor patch no and transmitting unit 130. Preferably, the linking interface 136 is a wireless interface; however, the linking interface 136 can alternatively be a wired connection. In a first variation, the linking interface 136 can include a first module that interfaces with a second module included in a mobile computing device 150 or other external element (e.g., wrist-borne mobile computing device, head-mounted mobile computing device), wherein data or signals (e.g., microsensor or transceiver outputs) are transmitted from the transmitting unit 130 to the mobile computing device 150 or external element over non-wired communications. The linking interface 136 of the first variation can alternatively implement other types of wireless communications, such as 3G, 4G, radio, or Wi-Fi communication. In the first variation, data and/or signals are preferably encrypted before being transmitted by the linking interface 136. For example, cryptographic protocols such as Diffie-Hellman key exchange, Wireless Transport Layer Security (WTLS), or any other suitable type of protocol can be used. The data encryption can also comply with standards such as the Data Encryption Standard (DES), Triple Data Encryption Standard (3-DES), or Advanced Encryption Standard (AES). In variations with data encryption, data can be unencrypted upon transmission to the mobile computing device 150 associated with the user. However, in an alternative variation, data can remain encrypted throughout transmission to a mobile computing device (associated with the user, not associated with the user) and unencrypted at another module of a processing subsystem 160 (e.g., unencrypted in the cloud), wherein information derived from analysis of the data can then be transmitted back to the mobile computing device associated with the user in a secure manner. In this variation, a user can thus pair his/her microsensor patch no with a mobile computing device unassociated with the user for transmission of encrypted data, and then later receive personalized body information at his/her own mobile computing device 150 after processing in the cloud.

In a second variation, the linking interface 136 is a wired connection, wherein the linking interface 136 includes a wired jack connector (e.g., a ⅛" headphone jack, a USB connection, a mini-USB connection, a lightning cable connection, etc.) such that the transmitting unit 130 can communicate with the mobile computing device 150 and/or an external element through a complementary jack of the mobile device and/or external element. In one specific example of the linking interface 136 that includes a wired jack, the linking interface is configured only to transmit output signals from the transmitting unit 130/microsensor patch no. In another specific example, the linking interface 136 is configured to transmit data to and from at least one element of transmitting unit 130/transdermal path 110 assembly and a mobile computing device 150. In this example, the linking interface 136 can transmit output signals into the mobile computing device 150 through an input of the jack of the mobile computing device 150 and can retrieve data from an output of the jack of the mobile computing device 150. In this example, the linking interface 136 can communicate with the mobile computing device 150 via inter-integrated circuit communication (I2C), one-wire, master-slave, or any other suitable communication protocol. However, the linking interface can transmit data in any other way and can include any other type of wired connection that supports data transfer between the transmitting unit 130 and/or microsensor patch 110, and the mobile computing device 150.

As noted above, the electronics subsystem 120 can include any other suitable module(s) and/or be configured in any other suitable manner. For instance, the electronics subsystem 120 can include or be in communication with an actuator configured to automatically perform an action (e.g., vibration, provision of a biasing force) that biases the microsensor into communication with interstitial fluid of the user, in response to detection of unsuitable impedance derived from comparison between an impedance signal and an impedance threshold condition.

1.1.3 System—Housing

The housing 190 supports the microsensor 116 and the electronics subsystem 120, and functions to facilitate robust coupling of the microsensor patch no to the user in a manner that allows the user to wear the microsensor patch no for a sufficient period of time (e.g., one week, one month, etc.). The housing 190 can also function to protect elements of the microsensor patch 110 from physical damage over the lifetime usage of the microsensor patch no. Preferably, at least one portion of the housing 190 is flexible to facilitate adhesion to the user and compliance with skin of the user as the user moves in his/her daily life; however, at least a portion of the housing 190 can alternatively be rigid in order to provide more robust protection against physical damage. In an embodiment where a portion of the housing 190 is flexible, other elements of the microsensor patch no can also be flexible (e.g., using a thin film battery, using flexible electronics, etc.) to facilitate adhesion to the user and compliance as the user moves about in his/her daily life. In one variation, the housing 190 can comprise a single unit that entirely houses the microsensor 116 and the electronics subsystem 120. In this variation, the housing 190 can be configured to couple to the user using any suitable coupling mechanism (e.g., adhesive coupling mechanism, strap-based coupling mechanism, etc.). However, in other variations, the housing 190 can alternatively be modular and comprise a set of portions, each portion configured to enable coupling of the microsensor 116 to the user and/or to house elements of the electronics subsystem 120. Modularity of the housing 190 can thus allow portions of the system 100 to be disposable and/or reusable.

Figure 9:
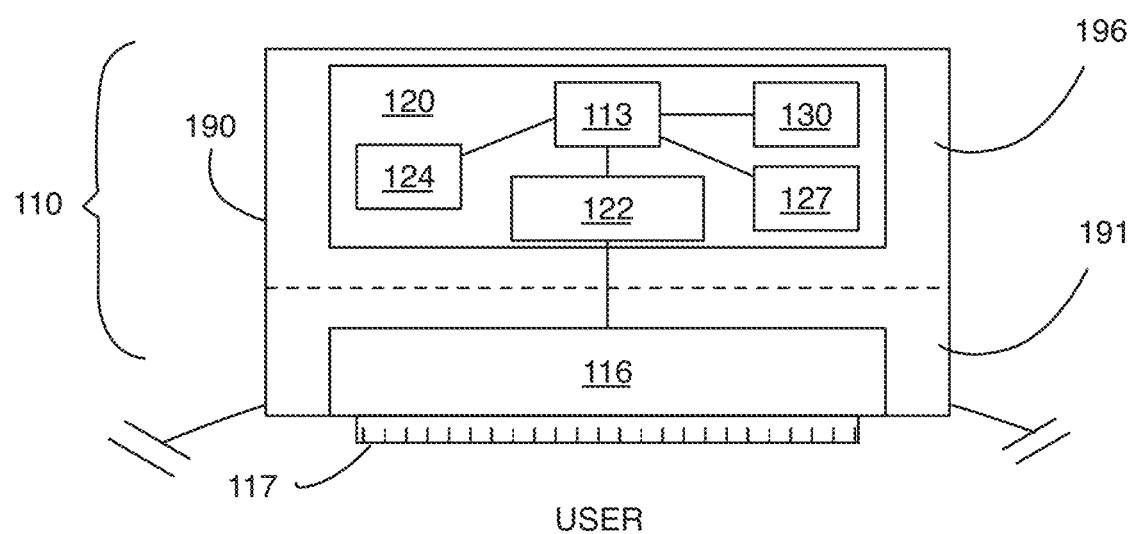
FIG. 9 depicts a variation of a housing in an embodiment of a system for monitoring body chemistry.
Figure 10A:
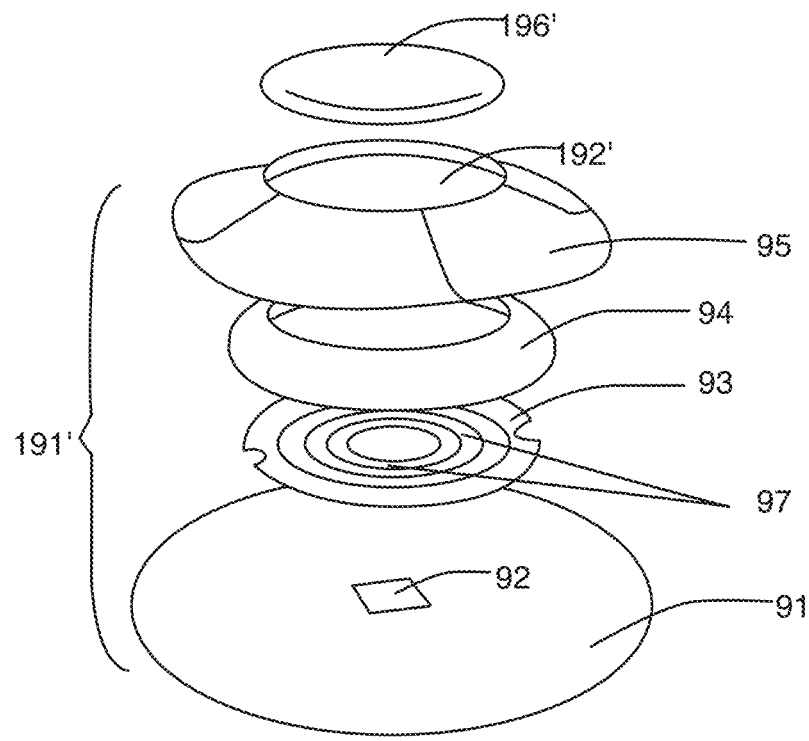
FIGS. 10A-10B depict specific examples of a housing in an embodiment of a system for monitoring body chemistry.
Figure 10B:
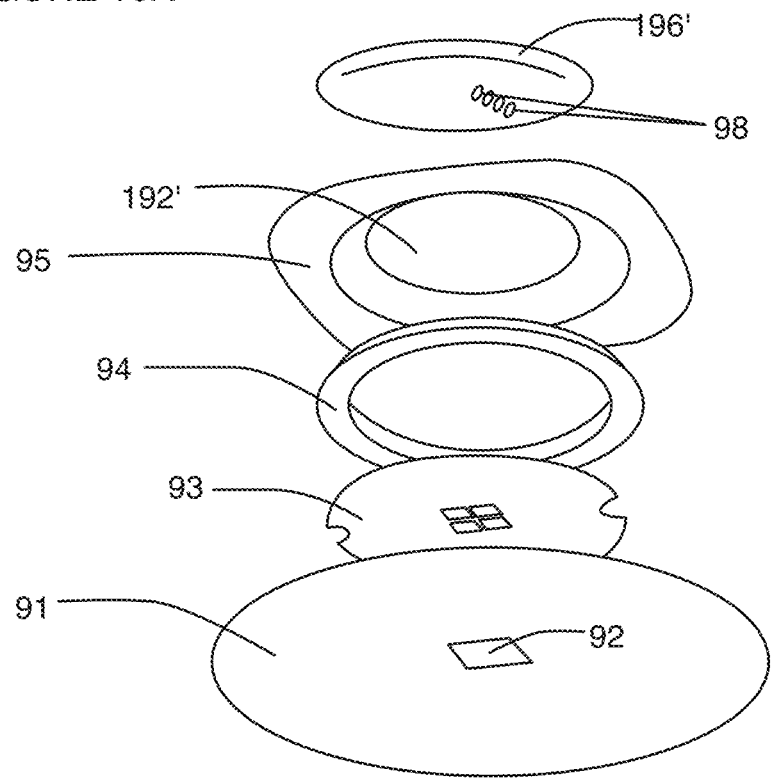
Figure 10C:
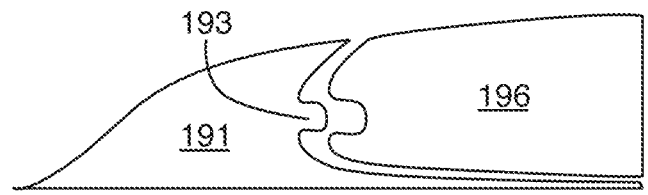
FIG. 10C depicts a specific portion of a housing in an embodiment of a system for monitoring body chemistry.

In one such modular variation of the housing 190, as shown in FIG. 9, the housing can comprise a first housing portion 191 and a second housing portion 196, wherein the first housing portion 191 is configured to facilitate coupling of filaments of the microsensor 116 to the user, and the second housing portion 196 is configured to house elements of the electronics subsystem 120 and to couple the electronics subsystem 120 to the microsensor 116 by way of the first housing portion 191. As such, the first housing portion 191 and the second housing portion 196 of this variation are preferably configured to mate with each other in a complementary manner (e.g., with a male-female coupling mechanism, with a magnetic coupling mechanism, with a latch-based coupling mechanism, with a lock-and-key based coupling mechanism, etc.). In a specific example, as shown in FIGS. 10A-10B, the first housing portion 191' includes an opening 192', and a second housing portion 196' is insertable into the opening of the first housing portion in a first configuration, wherein coupling between the first housing portion 191' and the second housing portion 196' provides a hermetic seal between the first housing portion 191 and the second housing portion 196. In more detail, as shown in FIG. 10C, the first housing portion 191 can include an o-ring 193 (e.g., an o-ring molded onto the material of the first housing portion) at a perimeter of the opening 192, and a perimeter region of the second housing portion 196 can include a recessed region 197 that interfaces with the o-ring 193 in a manner that provides a hermetic seal. In this specific example, the opening 192 and the second housing portion 196 each have substantially circular footprints; however, the opening 192 and the second housing portion 196 can additionally or alternatively have any other suitable footprints or be configured in any other suitable manner.

In the specific example, as shown in FIGS. 10A-10B, the first housing portion 191' can comprise an adhesive substrate 91 having a microsensor opening 92, a microsensor interface substrate 93 superior to the adhesive substrate and configured to pass the microsensor 92 through the microsensor opening 92, a coupling ring 94 configured to retain the position of the microsensor interface substrate 93 relative to the adhesive substrate 91 and to provide an interface for mating with the second housing portion 196, and a flexible cover 95 ensheathing the coupling ring 94, coupled to the adhesive substrate 91, and configured to maintain coupling between the adhesive substrate 191, the microsensor interface substrate 93, and the coupling ring 94. In relation to the configuration described above, the adhesive substrate 91 is configured to facilitate adhesion of the microsensor patch 110 to the user at an inferior surface of the adhesive substrate, and the flexible cover 95 is configured to provide the opening 192' that receives the second housing portion 192.

The second housing portion 196 of the specific example is rigid, and configured to form a shell about the electronics subsystem 120, while including openings that provide access for a set of contacts 98 that interface the electronics subsystem 120 with the microsensor interface substrate 93 when the first housing portion 191 is coupled to the second housing portion 196. In relation to the microsensor interface substrate 93 of the first housing portion 191, and in relation to a circular (or otherwise axially symmetric) configuration of an interface between the second housing portion 196 and the opening 192 of the first housing portion 191, the microsensor interface substrate 93 of the specific example can include a circular printed circuit board comprising a set of concentric ring contacts 97, as shown in FIG. 10A, that interface electronics of the second housing portion 196 with filaments of the microsensor 116. As such, the set of contacts 98 (e.g., digital contacts) of electronics of the second housing portion 196 can properly interface with the microsensor 116 in any rotational position of the second housing portion 196 within the first housing portion 191, as shown in FIG. 10B. In alternative variations of this specific example however, orientation-unspecific coupling between the first housing portion 191 and the second housing portion 196 can be achieved in any other suitable manner. In still alternative variations of this specific example, the first housing portion 191 and the second housing portion 196 can be configured to couple with a set orientation in order to ensure proper communication between the microsensor 116 and the electronics subsystem 120.

In variations of the housing 190 comprising a first housing portion 191 and a second housing portion 196, the first housing portion 191 and the second housing portion 196 can be coupled together and/or coupled to the user by way of a patch applicator 180, as described in further detail below. Furthermore, other variations of modularity can comprise any other suitable distribution of the microsensor 116 and elements of the electronics subsystem 120 across portions of the housing in any other suitable manner. For instance, in one such variation, the microsensor 116, the multiplexer 22, and the analog front end 93 of the electronics subsystem 120 can be coupled to a separate battery (e.g., a thin film battery) within a disposable portion of the housing 190, and other elements of the electronics subsystem 120 can be supported by a reusable portion of the housing 190. The system 100 can, however, comprise any other suitable distribution of elements across the housing 190 in a modular fashion.

1.2 System—Processing Subsystem

The processing subsystem 160 is in communication with the electronics subsystem 120 and functions to generate analyses pertaining to the user's body chemistry, and to transmit information derived from the analyses to the user at an electronic device associated with the user. As shown in FIG. 1, the processing subsystem 160 can be implemented in one or more of: a computer machine, a remote server, a cloud computing system, a microprocessor, processing hardware of a mobile computing device (e.g., smartphone, tablet, head-mounted mobile computing device, wrist-borne mobile computing device, etc.) and any other suitable processing system. In one variation, the processing subsystem 160 comprises a first module 161 configured to generate an analysis indicative of an analyte parameter of the user and derived from a signal stream from the microsensor 116 and an impedance signal from the electronics subsystem 120. Additionally, in this variation, the processing subsystem 160 comprises a second module 162 configured to render information derived from the analysis at an electronic device (e.g., mobile computing device 150) associated with the user, thereby facilitating monitoring of body chemistry of the user. In this variation, the modules of the processing subsystem 160 can be implemented in a hardware module and/or a software module. In variations, a software module 163 can be implemented, at least in part, as a native software application executing on a mobile computing device 150 associated with the user, wherein the user has a user account associated with the native software application.

In more detail, the software module 163 functions to analyze an output provided by the transmitting unit 130 of the electronics subsystem 120, and to communicate an analysis of the output back to the user, so that the user can monitor his/her body chemistry. Preferably, the software module 163 analyzes at least one analyte parameter in order to determine a metric providing information about a user's body chemistry. In one variation, the software module can determine that a body analyte parameter (e.g., glucose level) of the user is too low or less than ideal, and facilitate a behavior change in the user by providing a body chemistry metric indicating a hypoglycemic state. In this variation, the software module can additionally determine that the body analyte parameter (e.g., glucose level) of the user is within a proper range based on a determined metric. The software module of this variation can additionally determine that the body analyte parameter (e.g., glucose level) of the user is too high and facilitate a behavior change in the user by providing a body chemistry metric indicating a hyperglycemic state.

In another example, the software module can analyze an output provided by the transmitting unit 130 based on a set of parameters for multiple analytes characterizing a user's body chemistry, at a set of time points, and determine at least one metric based on the set of parameters at the set of time points. The software module can then determine and output at least one of a temporal trend in a metric, a temporal trend in an analyte parameter, absolute values of a metric, changes in value of a metric, absolute values of an analyte parameter, and changes in value of an analyte parameter. The software module 163 in this example can further be configured to communicate a suggestion to the user based on an analysis determined from the set of parameters for multiple analytes.

The software module preferably incorporates at least one of user health condition, user characteristics (e.g., age, gender, ethnicity), and user activity in analyzing an output provided by the transmitting unit 130. In one specific example, if a user sets a desired body glucose level range, which is entered into the software module, the software module can be configured to facilitate provision of alerts notifying the user of short-term risks (e.g., diabetic crash), long-term risks (e.g., worsening diabetic condition), and risk of exiting the desired body glucose level range. In another specific example, the software module can compare analyte parameters and/or a metric characterizing the user's body chemistry to other users with similar health conditions or characteristics (e.g., age, gender, ethnicity). In yet another example, the software module can be able to correlate at least one analyte parameter or metric to a user activity, such that the user is provided with information relating a value of the analyte parameter and/or metric to an activity that he or she has performed. The software module can additionally or alternatively provide an analysis that includes any other health- and/or user-related information that can be useful in treating, maintaining, and/or improving a health condition of a user.

Figure 11A:
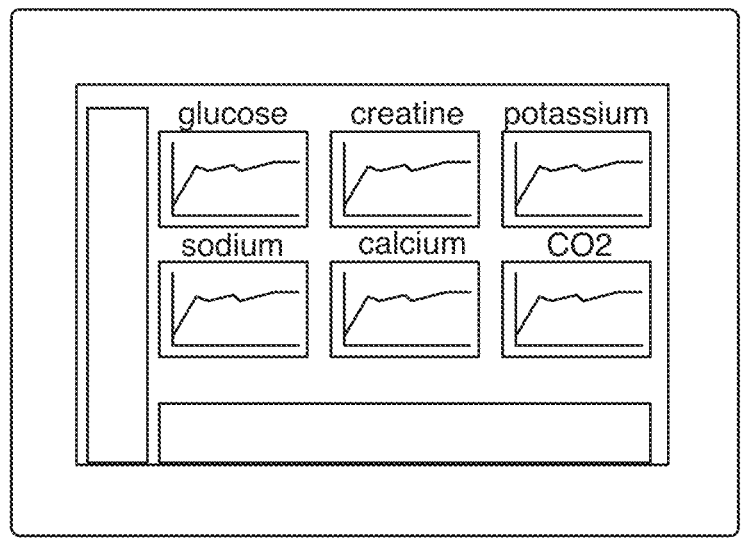
FIGS. 11A-11B depict examples of user interfaces implemented using a software module in an embodiment of a system for monitoring body chemistry.
Figure 11B:
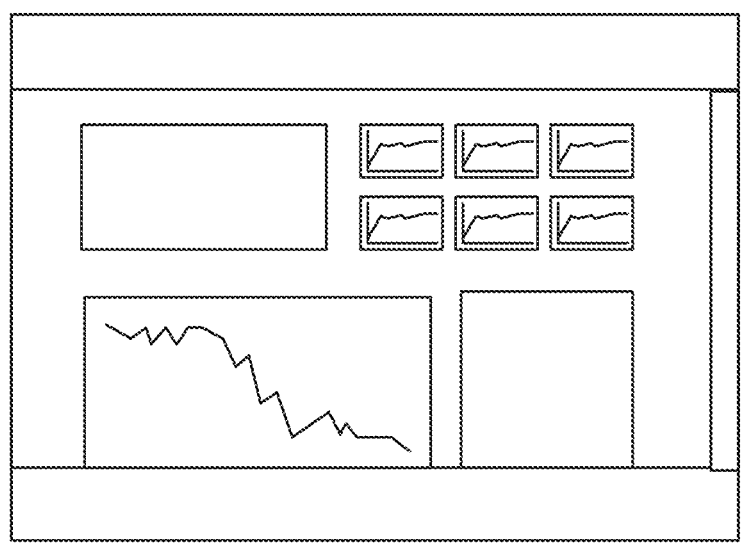

As shown in FIGS. 1, 11A, and 11B, the software module can be implemented, at least in part, as an application executable on a mobile computing device 150. As described above, the mobile computing device 150 is preferably a smartphone but can also be a tablet, laptop computer, PDA, e-book reader, head-mounted computing device, smartwatch, or any other mobile device. The software module can alternatively be an application executable on a desktop computer or web browser. The software module preferably includes an interface that accepts inputs from the user (e.g., user health condition, user characteristics, user activity), and uses these inputs in analyzing an output provided by the transmitting unit 130. Preferably, the software module also includes an interface that renders an analysis based on sensed analytes and/or user inputs in some form. In an example, the software module includes an interface that summarizes analyte parameter values in some manner (e.g., raw values, ranges, categories, changes), provides a trend (e.g., graph) in at least one analyte parameter or body chemistry metric, provides alerts or notifications, provides additional health metrics, and provides recommendations to modify or improve body chemistry and health metrics. In another example, the software module can implement two interfaces: a first interface accessible by a user, and a second interface accessible by a health care professional servicing the user. The second interface can provide summarized and detailed information for each user that the health care professional interacts with, and can further include a message client to facilitate interactions between multiple users and the health care professional. The software module can additionally or alternatively access a remote network or database containing health information of the user. The remote network can be a server associated with a hospital or a network of hospitals, a server associated with a health insurance agency or network of health insurance agencies, a server associated with a third party that manages health records, or any other user- or heath-related server or entity. The software module can additionally or alternatively be configured to accept inputs from another entity, such as a healthcare professional, related to the user.

The software module 163 can additionally or alternatively execute fully or in part on a remote server. In a first variation, the software module can be a cloud-computing-based application that performs data analysis, calculations, and other actions remotely from the mobile computing device 150. In one example of the first variation, the mobile computing device 150 can receive an output of the transmitting unit 130 via the linking interface 136 and then transfer the output to the remote server upon which the software module executes. In the first variation, signals are preferably transferred via a wireless connection, such as a Bluetooth connection, 3G or 4G cellular connection, and/or via a Wi-Fi internet connection. In another example of the first variation, a mobile computing device 150 can function to transmit data to and/or receive data from the software module. In a second variation, the software module can include a first software component executable on a mobile computing device 150, such as an application that manages collection, transmission, retrieval, and/or display of data. In the second variation, the software module can further include a second software component that executes on the remote server to retrieve data, analyze data, and/or manage transmission of an analysis back to the mobile computing device 150, wherein the first software component manages retrieval of data sent from the second software component and/or renders of a form of the analysis on a display of the mobile computing device 150. However, the software module can include any number of software components executable on any mobile computing device 150, computing device, and/or server and can be configured to perform any other function or combination of functions.

Figure 12A:
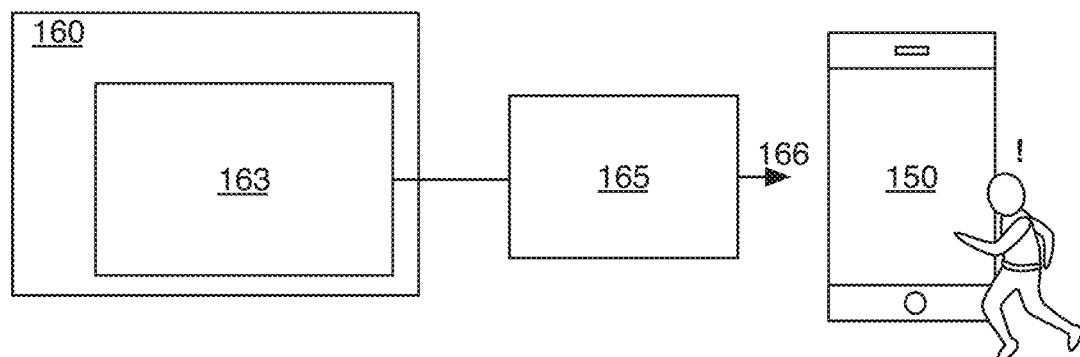
FIG. 12A depicts a notification module of an embodiment of a system for monitoring body chemistry.

As shown in FIG. 12A, the software module 163 can further be integrated with a notification module 165 configured to provide an alert or notification to a user and/or health care professional based on the analysis of the output. The notification module 165 functions to access an analysis provided by the software module and to control transmission of a notification 166 to at least one of a user and a healthcare profession interacting with the user. In one variation, the notification module 165 receives an analysis of the software module being executed on a mobile computing device 150, and generates a notification 166 based upon the analysis. In this variation, a form of the analysis is preferably transmitted from the software module, executing on the mobile computing device 150, to the notification module 165, wherein the mobile computing device 150 accesses the analysis either from the software module executing on the mobile computing device 150 or from the software module executing on a remote server and in communication with the mobile computing device 150. The notification module 165 preferably controls transmission of the notification 166 to the user, such as by triggering a display of the mobile computing device 150 to display a form of the notification, or by generating and/or transmitting an email, SMS, voicemail, social media platform (e.g., Facebook or Twitter) message, or any other message accessible by the user and which contains the notification 166. The notification module 165 can also convey the notification 166 by triggering a vibration of the mobile device 160, and/or by altering the state (i.e., ON or OFF) of one or more light sources (e.g., LEDs) of the mobile computing device 150. However, the notification module 165 can alternatively manage the transmission of any other information and function in any appropriate manner.

The notification 166 preferably contains information relevant to a body chemistry status of the user. The notification 166 can additionally include an explicit directive for the user to perform a certain action (e.g., eat, rest, or exercise) that affects the body chemistry of the user. Therefore, the notification 166 preferably systematically and repeatedly analyzes a body chemistry status of the user based on at least one analyte parameter of the user and provides and alert and/or advice to manage and monitor a user's body chemistry substantially in real time. In one example, the notification 166 can further include information related to what or how much to eat, where and how long to run, level of exertion, and/or how to rest and for how long in order to appropriately adjust body chemistry. In other examples, the notification 166 can include any appropriate information relevant to monitoring a body chemistry metric of the user.

Figure 12B:
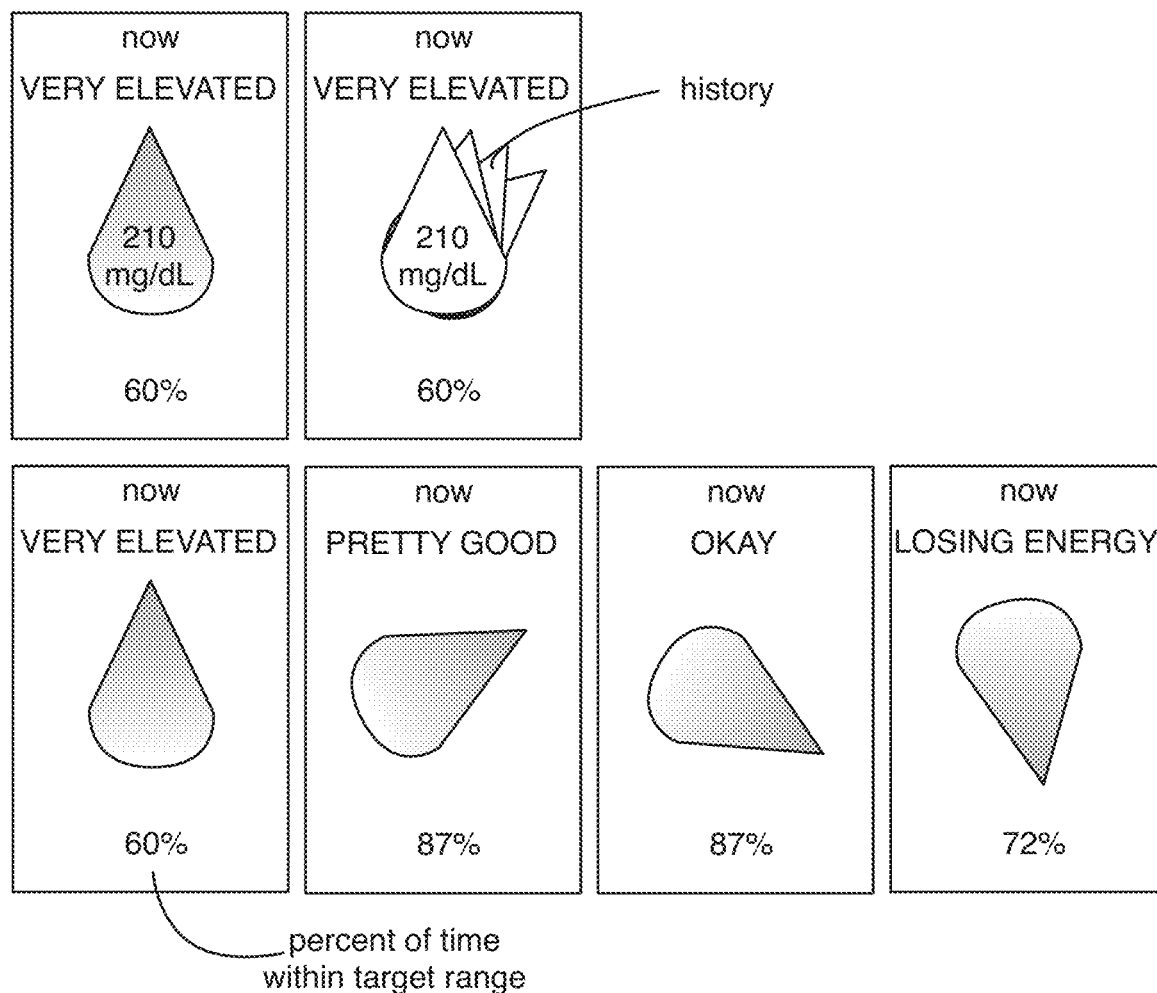
FIGS. 12B-12C depict specific examples of notifications in an embodiment of a system for monitoring body chemistry.

In still other examples, as shown in FIG. 12B, the notification 166 can indicate one or more of: a current level of a measured analyte (e.g., represented in hue, represented in saturation, represented in intensity, etc. of a graphical rendering); a trending direction for the level of the measured analyte (e.g., represented in a feature gradient within a graphical rendering); a lower bounding level and an upper bounding level between which the level of the measured analyte is traversing; a trending direction of a level of a measured analyte (e.g., represented in an arrow of a graphical rendering); a quantification of a level of a measured analyte (e.g., represented as rendered text); a summary of a level of a measured analyte (e.g., represented as rendered text); a percent of time within a time duration (e.g., one day) that the level of the measured analyte is within a target range (e.g., healthy range); and historical behavior of a level of a measured analyte (e.g., represented as historical "ghosting" of a rendering based upon a previous analyte level).

Figure 12C:
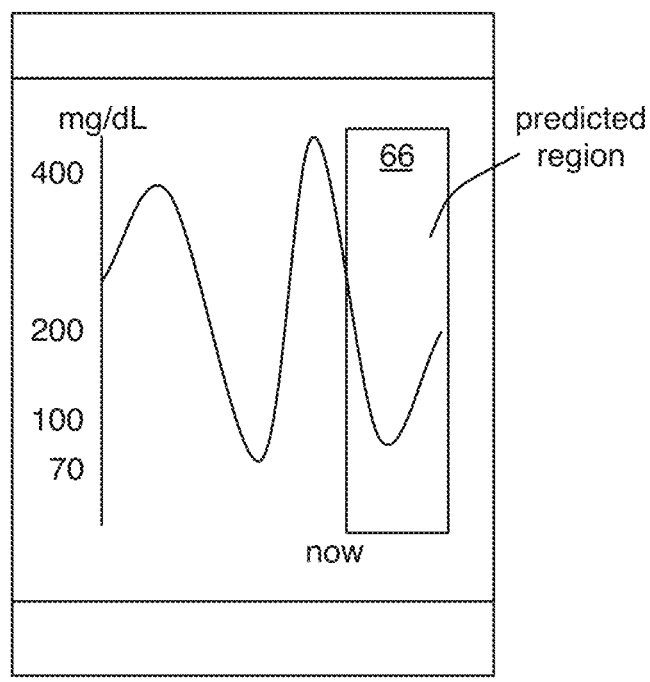

Additionally or alternatively, in still other examples, as shown in FIG. 12C, the notification 166 can include a graphical rendering that shows analyte data from past to present using a line graph representation, wherein an amount (e.g., concentration) of the analyte is represented along a first axis and time is represented along a second axis. In these examples, the graphical rendering can further include a "predicted region" based upon the analysis of the processing subsystem 160, wherein the predicted region 66 depicts a prediction of where the analyte level will be at a future time point, and a width of the predicted region 66 indicates confidence in the prediction.

Figure 13:
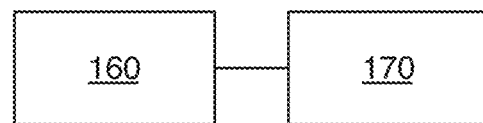
FIG. 13 depicts communication between a processing subsystem and a storage module in an embodiment of a system for monitoring body chemistry.

In relation to the processing subsystem 160 and analyses generated at the processing subsystem 160, the processing subsystem 160 can be coupled to or comprise a data storage unit 170, as shown in FIG. 13. The data storage unit 170 functions to retains data, such as an analysis provided by a software module, a notification 166, and/or any other output of any element of the system 100. The data storage unit 170 can be implemented with the microsensor patch 110, transmitting unit 130, mobile computing device 150, personal computer, web browser, external server (e.g., cloud), and/or local server, or any combination of the above, in a network configured to transmit, store, and receive data. Preferably, data from the data storage unit 170 is automatically transmitted to any appropriate external device continuously; however, data from the data storage unit 170 can alternatively be transmitted only semi-continuously (e.g., every minute, hourly, daily, or weekly). In one example, data generated by any element can be stored on a portion of the data storage unit 170 when the linking interface 136 is not coupled to an element external to the microsensor patch no/transmitting unit 130 assembly. However, in the example, when a link is established between the linking interface 136 and an external element, data can then be automatically transmitted from the storage unit 170. In other examples, the data storage unit 170 can alternatively be prompted to transmit stored data by a user or other entity. Operation modes related to device pairing and information transfer are further described in relation to the base station of Section 1.4 below.

1.3 System—Applicator

Figure 14A:
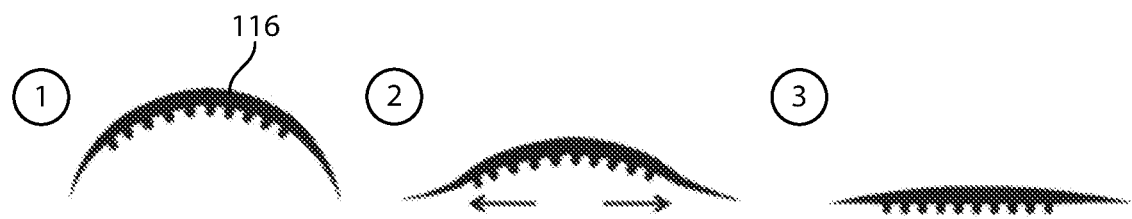
FIGS. 14A-14C depict examples of an arch application method and an end-to-end application method, respectively, in an embodiment of a system for monitoring body chemistry.
Figure 14B:
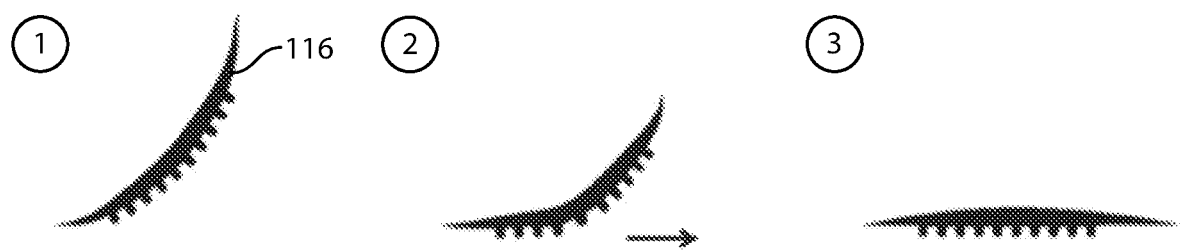
Figure 14C:
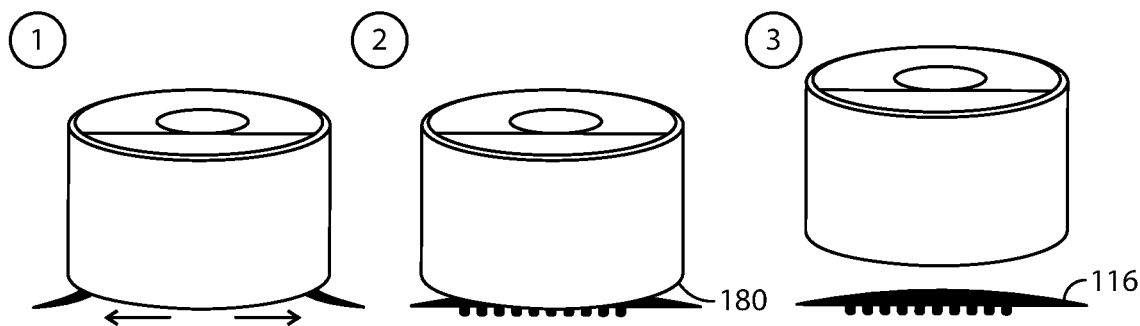
Figure 15A:
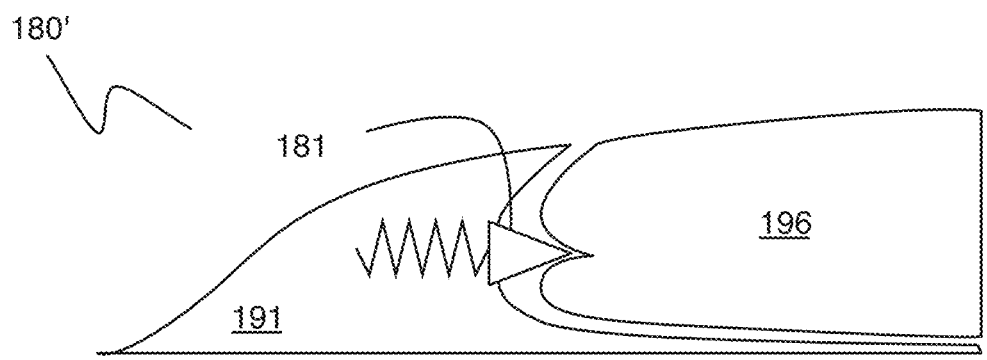
FIGS. 15A-15B depict variations of a patch applicator in an embodiment of a system for monitoring body chemistry.

As shown in FIG. 1, the system 100 can further comprise a patch applicator 180, which functions to facilitate application of at least one of the microsensor patch 110 and the transmitting unit 130. The patch applicator 180 preferably accelerates the a portion of the housing with the microsensor 116 toward skin of the user, thereby causing the microsensor 116 to penetrate skin of the user and sensing regions of the microsensor to access interstitial fluid of the user. However, the patch applicator 180 can additionally or alternatively facilitate coupling of the microsensor 116 to the user using one or more of: skin stretching, skin permeabilization, skin abrasion, vibration, and/or any other suitable mechanism, variations of which are shown in FIGS. 14A-14C. In a first variation, as shown in FIG. 15A, the patch applicator 180' can be incorporated into a first housing portion 191 of a housing 190 of the system 100 and can comprise an elastic pin 181 (e.g., spring-loaded pin) configured to complement a recess of a second housing portion 196. In this variation, a normal force applied to a broad surface of the second housing portion 196 initially causes the elastic pin 181 to retract, and rebounding of the elastic pin 181 into the recess of the second housing portion 196 biases and accelerates the microsensor 116 into the skin of the user.

Figure 15B:
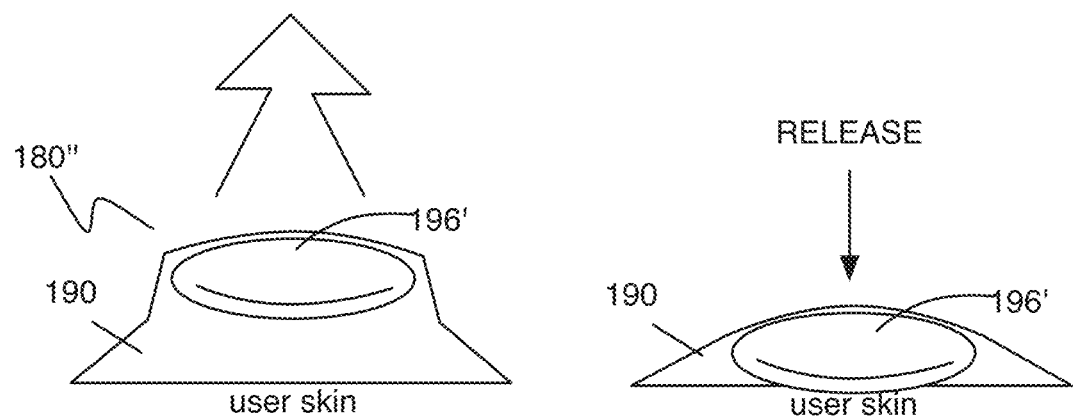

In a second variation, as shown in FIG. 15B, the patch applicator 180" implements elastic portions of the housing 190, which can be used to retract a housing portion with the microsensor 116 and to release the housing portion, thereby accelerating the microsensor 116 into skin of the user.

Figure 16A:
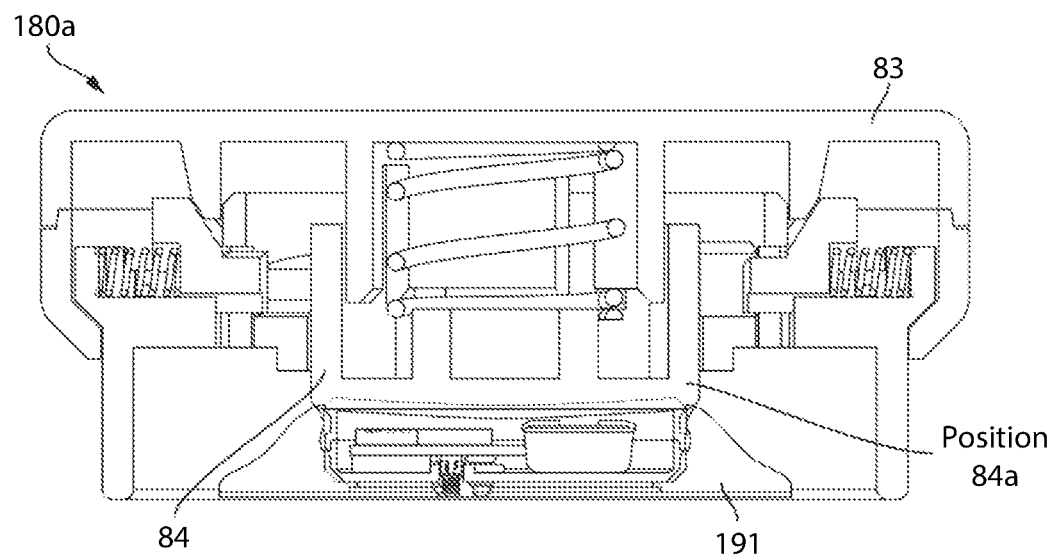
FIGS. 16A-16D depict a first specific example of a patch applicator in an embodiment of a system for monitoring body chemistry.
Figure 16B:
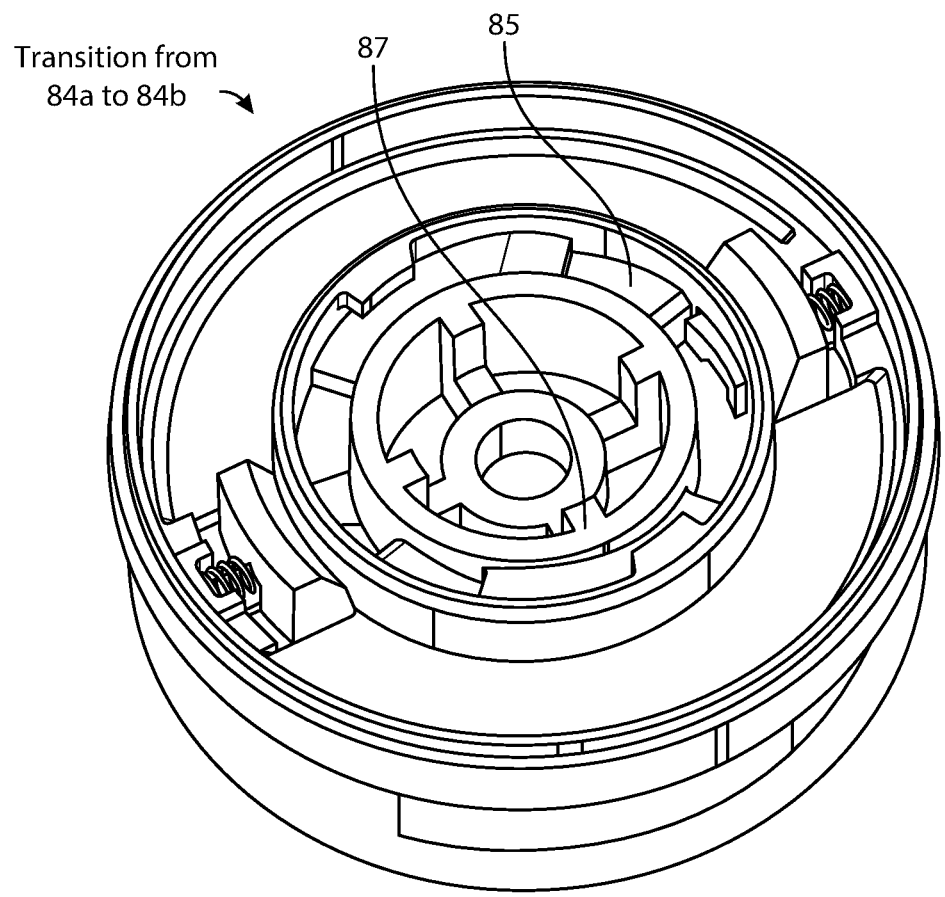
Figure 16C:
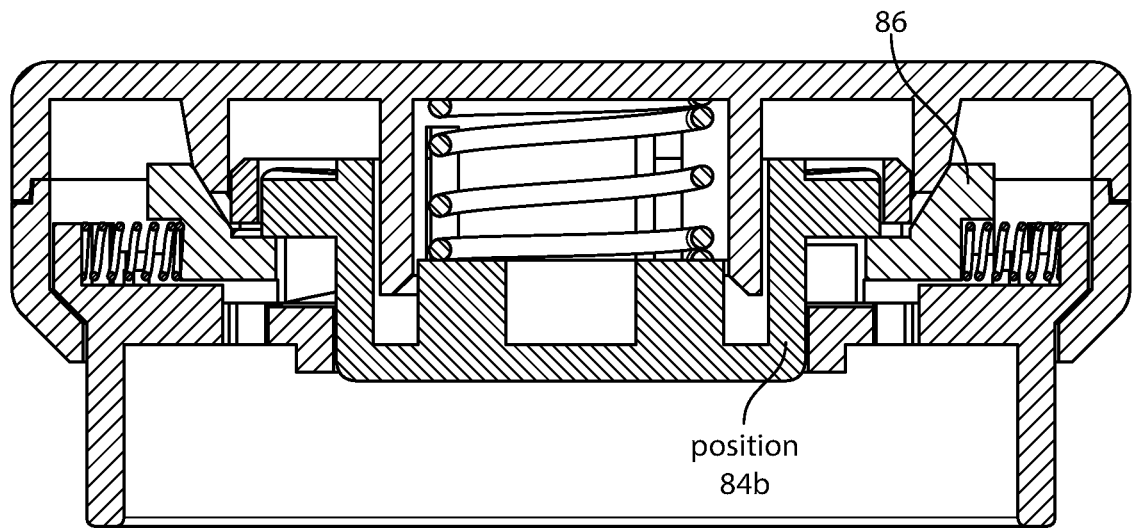
Figure 16D:
Figure 16D:
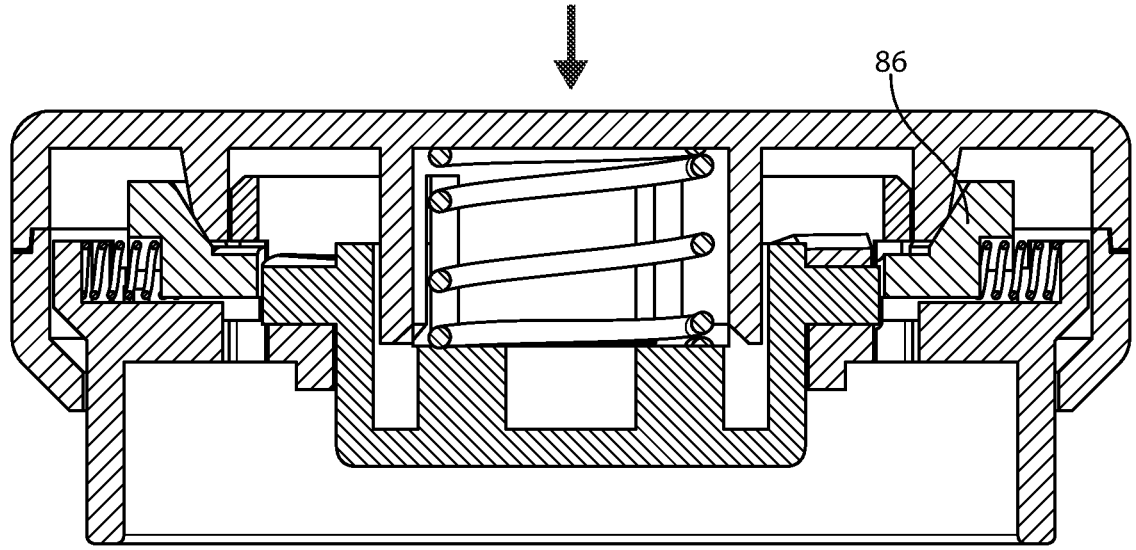

In a third variation, the patch applicator cooperates with a first housing portion 191 and a second housing portion 196, wherein the patch applicator comprises a first applicator portion configured to surround the housing 190 and interface with the second housing portion 196, and a second applicator portion configured to accelerate the second housing portion toward skin of the user. In a first specific example of the third variation, as shown in FIG. 16A, the patch applicator 180a comprises a ram-and-catch mechanism, wherein twisting of a rotatable component 83 of the patch applicator 180a transitions a plunger 84 of the patch applicator 180a from a resting configuration 84a to a loaded configuration 84b, as shown in FIGS. 16B and 16C, and pushing of the rotatable component 83 of the patch applicator 180a releases the plunger 84 back to the resting configuration 84a (as shown in FIG. 16D), thereby accelerating the microsensor 116 toward skin of the user during application of the microsensor patch 110 to the user. In more detail, in the first specific example, twisting of the rotatable component 83 transitions the plunger 84 along ramped surfaces 85 of the patch applicator 180a to the loaded configuration 84a, where the plunger 84 rests on triggers 86 of the patch applicator 180a. Then, as shown in FIG. 16D, pressing of the rotatable component 83 provides an outward biasing force on the triggers 86 (e.g., due to wedge-shaped morphology of the triggers that interacts with a complementary portion of the rotatable component 83), thereby releasing the plunger 84 to the resting configuration 84a. In this specific example, a set of ribs 87 coupled to a wall of the patch applicator 180 surrounding the plunger 84 maintain plunger alignment.

Figure 17:
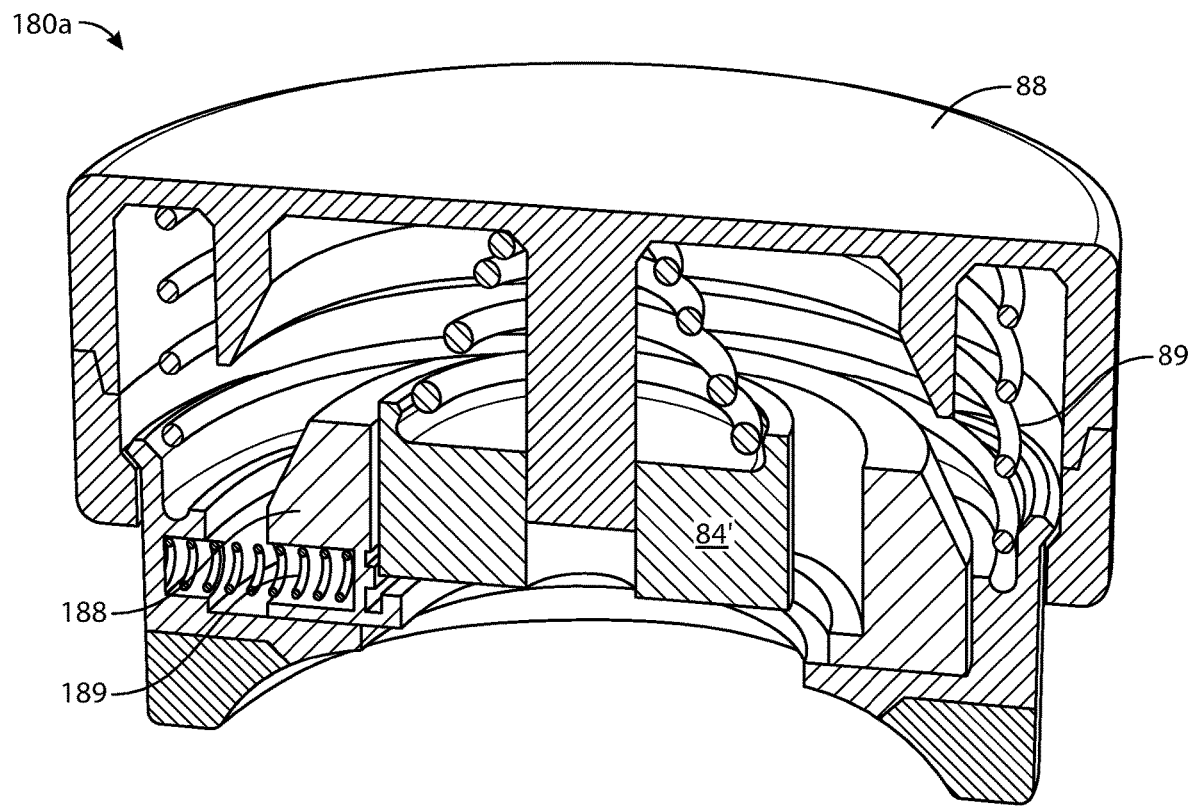
FIG. 17 depicts a second specific example of a patch applicator in an embodiment of a system for monitoring body chemistry.

In a second specific example of the third variation, as shown in FIG. 17, the patch applicator 180b comprises an elastic component 89 housed within and coupled to a translating component 88 of the patch applicator 180b, wherein the translating component 88 comprises a plunger 84' and is configured to translate along a first axis. The patch applicator 180b further comprises a trigger 188 coupled to a biasing spring 189 and configured to translate along a second axis perpendicular to the first axis, between a holding position 188a and a releasing position 188b. In the second specific example, the translating component 88 is biased in holding position 188a, and pushing of the translating component 88 places a lateral biasing force on the trigger 188 against the biasing spring 189 (e.g., due to wedge-shaped morphology of the trigger 188 that interacts with a complementary portion of the translating component 88), thereby releasing the plunger 84' to accelerate the microsensor 116 toward skin of the user. In pushing the translating component 88, compression of the elastic component 89 creates a reverse biasing force that automatically releases the translating component 88 toward the resting configuration 88a.

The patch applicator 180 can alternatively be configured to receive the microsensor patch 110, to stretch the skin of the user isotropically in two dimensions to facilitate application, and to push the microsensor patch no/transmitting unit 130 assembly onto the user's stretch skin. Still alternatively, the patch applicator 180 can include any other suitable applicator, variations and examples of which are described in U.S. App. No. 62/025,174 entitled "System for Monitoring Body Chemistry" and filed on 16 Jul. 2014. Still other variations of the system 100 can entirely omit a patch applicator 180.

1.4 System—Base Station

Figure 18A:
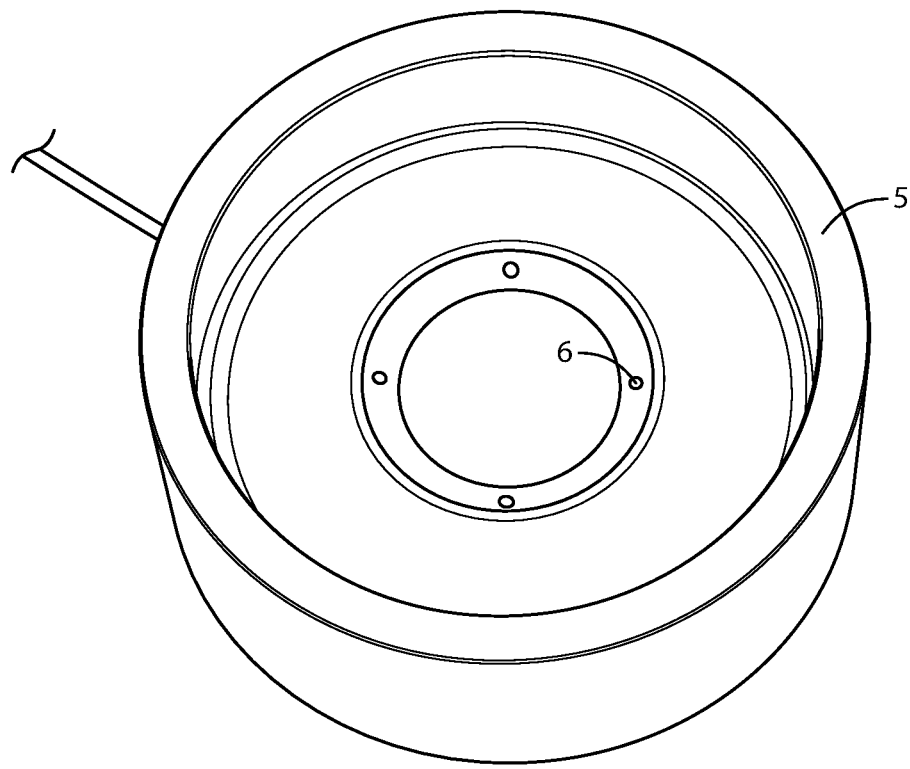
FIGS. 18A-18B depict a specific example of a base station in an embodiment of a system for monitoring body chemistry.
Figure 19:
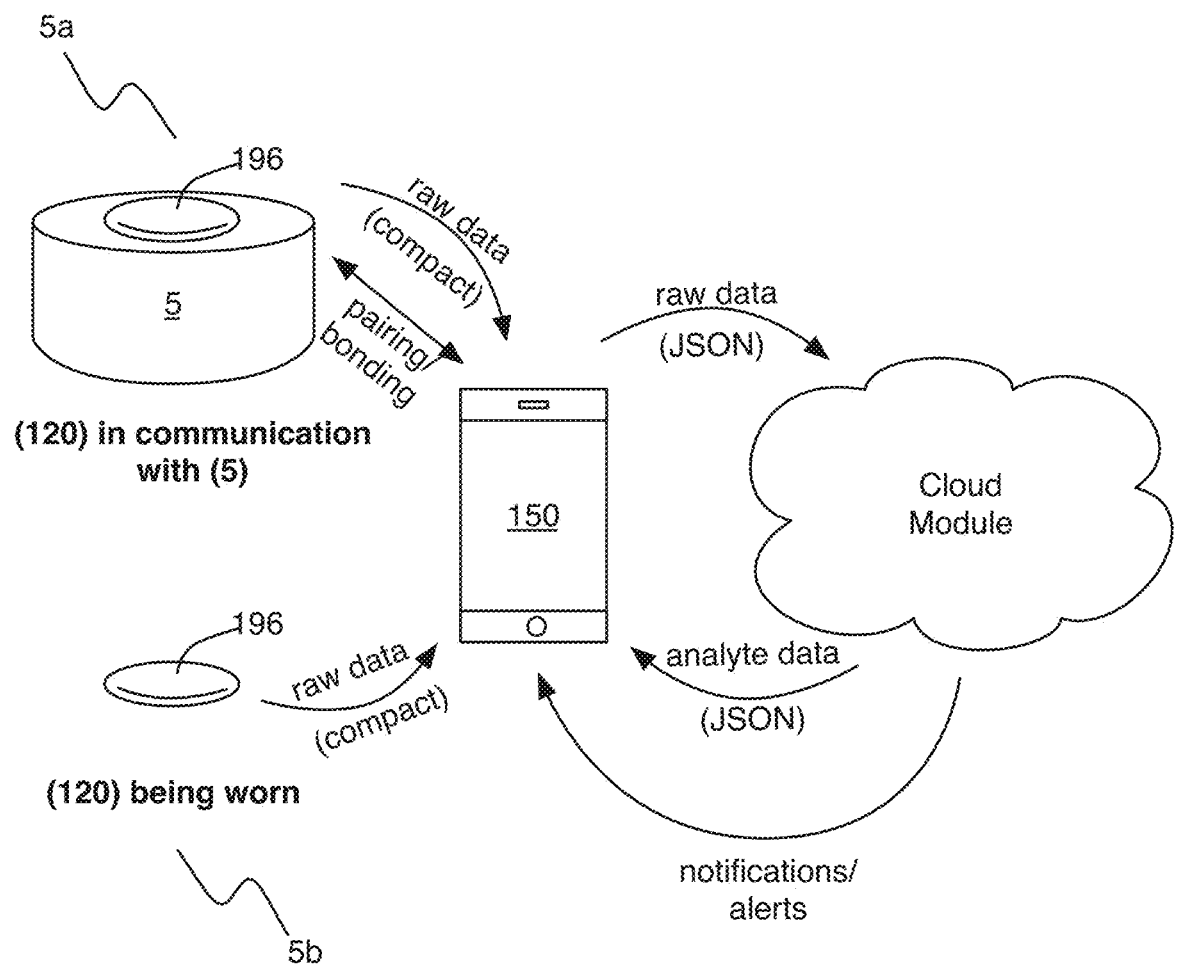
FIG. 19 depicts operation modes of components of an embodiment of a system for monitoring body chemistry.

As shown in FIG. 1, the system can include a base station 5 that functions to receive the microsensor patch no (e.g., within a second housing portion 196). In receiving the microsensor patch no, the base station 5 can include alignment elements 6 (e.g., protrusions, recesses, magnetic alignment elements, etc.) that facilitate alignment of the microsensor patch no within the base station, as shown in FIG. 18A. The base station 5 can additionally or alternatively facilitate charging of a rechargeable battery of the microsensor patch 110 by including elements that generate an electromagnetic field that interacts with a charging coil coupled to the battery, thereby charging the battery 138. The base station 5 can additionally or alternatively be used to transition the microsensor patch between different operational states, in relation to data transfer between the microsensor patch no, a mobile computing device 150 associated with the user, and modules of a processing subsystem 160 (e.g., cloud module) as shown in FIG. 19. In a first operation mode 5a, the transmitting unit 130 of the microsensor patch 110 and the mobile computing device 150 can pair/bond only when the second housing portion 196 of the microsensor patch 110 is in communication with the base station 5 (e.g., aligned within the base station 5). Thus, in the first operation mode 5a, the microsensor patch 110 can transmit and receive data (e.g., compact raw data compounded into a plurality of bits over Bluetooth communication). In a second operation mode 5b wherein the microsensor patch 110 is not in communication with the base station 5, the microsensor patch 110 can be configured to only transmit data (but not receive data), thereby reducing energy usage, preventing man-in-the-middle attack, and preventing tampering. As such, the second operation mode 5b prevents reading of data from the microsensor patch 110 by a fraudulent entity, without gaining physical access to the microsensor patch 110.

The operation modes of the system 100 enabled by the microsensor patch, the base station 5, the mobile computing device 150, and the processing subsystem 160 are further detailed in FIG. 19. In relation to pairing with the microsensor patch 110 in the first operation mode 5a, the mobile computing device 150 functions to provide one or more of: data relay, data visualization, data storage, notification, and action functions (e.g., as described in relation to the software module 163 described above). In communicating information between the mobile computing device 150 and a cloud module of the processing subsystem 160, the mobile computing device 150 can be configured to transmit raw data in Javascript Object Notation (JSON) format (or any other suitable format) to be processed in the cloud, and analyte data, notifications, and alerts (e.g., as derived from an analysis) can be transmitted back to the mobile computing device 150 in JSON format (or any other suitable format). The cloud module of the processing subsystem 160 can thus serve to enable authentication of the user (e.g., in association with a user account of a native application) and/or data, data storage, data processing, notification, and prediction functions, as described in relation to the processing subsystem 160 described above. Thus, the system 100 is configured for fault tolerance, wherein the microsensor patch 110 stores data when faulty operation of the mobile computing device 150 occurs, and failure of the processing subsystem 100 results in data storage at the mobile computing device. The system 100 can, however, be configured in any other suitable manner.

Figure 18B:
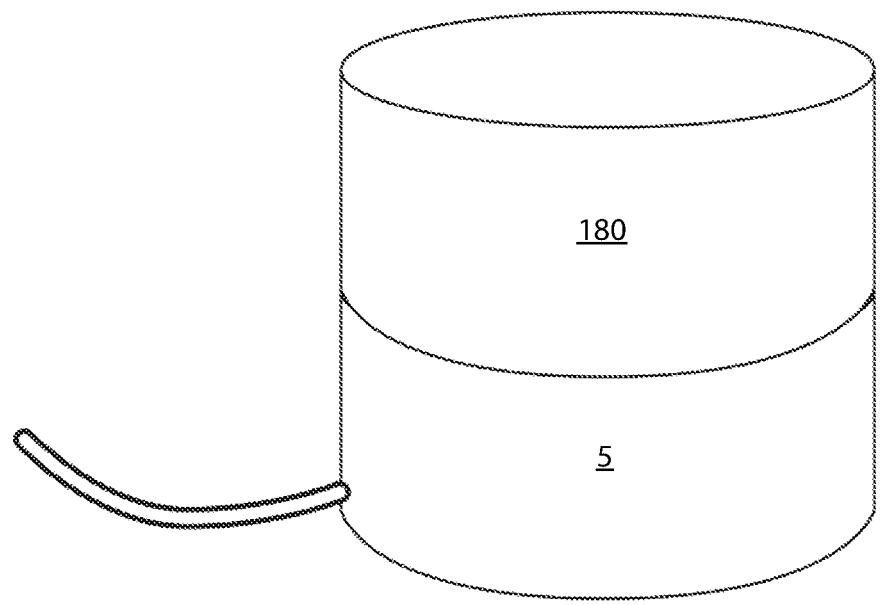

As shown in FIG. 18B, the base station 5 and the patch applicator 180 can be configured to couple together, thus facilitating portability of the base station 5 and patch applicator 180. However, the base station 5, patch applicator 180, and microsensor no can alternatively be configured to couple or not couple together in any other suitable manner.

1.5 System—Calibration

The microsensor patch 110 is preferably calibrated to prevent signal degradation and to mitigate the effects of transient effects experienced during analyte sensing. The primary sensing mechanism is potentiometric for small analytes (e.g., potassium, sodium, calcium), and amperometric for large molecules (e.g., glucose, lactic, creatinine). In a first variation, the microsensor patch no passively detects analytes by detecting an impedance and/or capacitance change, as well as a voltage change when an analyte or analyte concentration contacts the microsensor 116. Calibration can occur by normalizing sensing measurements relative to a grounded portion of the microsensor 116, such as a reference electrode.

In a second variation, the microsensor patch 110 can implement active impedance calibration, wherein a drive voltage is implemented by the electronics subsystem in of the microsensor patch 110, and voltage and impedance and/or capacitance changes are detected. The drive voltage is preferably applied in a sinusoidal pattern, but can alternatively be applied in any appropriate pattern. In the second variation, sensed analytes or analyte concentrations are characterized by changes in impedance, and noise is characteristically distinguished from analyte detection by monitoring changes in voltage unaccompanied by changes in impedance or capacitance. The second variation thus employs a conductometric measurement to calibrate the microsensor patch 110. Impedance measurements can also be used to address shift in a reference electrode (e.g., in the first variation described above).

In a third variation, the microsensor patch 110 can employ injection of a volume of a calibration solution with a known concentration of at least one analyte, in order to calibrate the microsensor patch 110. In an example of the third variation, the calibration solution can have a known concentration of at least one analyte, such that changes (e.g., changes in electrical parameters) detected by the microsensor patch 110 in response to the calibration solution can be used to normalize measurements resulting from sensed analytes or analyte concentrations occurring after injection of the volume of calibration solution. In the third variation, the calibration solution can be injected automatically and periodically over the lifetime usage of the transdermal patch; however, the calibration solution can alternatively be injected when prompted by a user or other entity.

In a fourth variation, the microsensor patch 110 can include a membrane comprising a known concentration and/or release profile of at least one analyte, in order to calibrate the microsensor patch no. In an example of the fourth variation, the membrane can have a known concentration and release profile of at least one analyte, such that changes (e.g., changes in electrical parameters) detected by the microsensor patch 110 in response to the membrane can be used to normalize measurements resulting from sensed analytes or analyte concentrations. In the fourth variation, the membrane can be a degradable membrane, such that degradation of the membrane over time releases analytes from the membrane. Alternatively, the membrane can be manufactured with specific porosity, contributing to a certain analyte release profile.

In a fifth variation, the microsensor patch no can include a coating or a cap comprising a soluble species (e.g., analyte/ion) with a well-known solubility, in order to calibrate the microsensor patch no. In an example of the fifth variation, the soluble species maintains a known concentration of the species within the vicinity of a filament that can be used to normalize and/or calibrate a signal. Examples of soluble species include low solubility, biocompatible calcium salts, such as calcium carbonate, calcium phosphate, and dicalcium phosphate for calcium sensing. Other suitable soluble species can be used to calibrate other analytes.

In alternative variations, the microsensor patch 110 can use any other suitable calibration method. For instance, the transdermal patch can be pre-staged, prepped, loaded, or activated to have a set calibration state enabling calibration of the system after application to the user within a desired period of time (e.g., an 85 mg/dl calibration state equilibrated after insertion within a period of 2 hours).

As a person skilled in the art will recognize from the previous detailed description and from the figures and claims, modifications and changes can be made to the described embodiments, variations, and examples of the system 100 without departing from the scope of the system 100.

2. Method

As shown in FIG. 20, a method 200 for monitoring body chemistry of a user comprises: receiving a second housing portion into an opening of a first housing portion S210, the first housing portion supporting a microsensor including a first working electrode, a second working electrode, a reference electrode, and a counter electrode, and the second housing portion supporting an electronics subsystem configured to receive a signal stream from the microsensor; after interfacing with the second housing portion, accelerating the second housing portion toward skin of the user S220, thereby delivering sensing regions of the microsensor into interstitial fluid of the user; generating an impedance signal, from two of the first working electrode, the second working electrode, the reference electrode, and the counter electrode, in response to applying a voltage, near a shifted potential different than a reference potential of the reference electrode S230, wherein the shifted potential is associated with a signal conditioning module of the electronics subsystem; at a processing system in communication with the electronics subsystem, receiving the signal stream and the impedance signal S240; at the processing system, generating an analysis indicative of an analyte parameter of the user and derived from the signal stream and the impedance signal S250; and transmitting information derived from the analysis to an electronic device associated with the user, thereby facilitating monitoring of body chemistry of the user S260.

The method 200 functions to provide continuous monitoring of a user's body chemistry through reception and processing of signals associated with of one or more analytes present in the body of the user, and to provide an analysis of the user's body chemistry to the user and/or an entity (e.g., health care professional, caretaker, relative, friend, acquaintance, etc.) associated with the user. Alternatively, the method 200 can function to detect a user's body chemistry upon the user's request or sporadically, and/or can provide an analysis of the user's body chemistry only to the user. The method is preferably implemented, at least in part, using an embodiment, variation, or example of elements of the system 100 described in Section 1 above; however, the method 200 can additionally or alternatively be implemented using any other suitable system.

Variations of the system 100 and method 200 include any combination or permutation of the described components and processes. Furthermore, various processes of the preferred method can be embodied and/or implemented at least in part as a machine configured to receive a computer-readable medium storing computer-readable instructions and/or in the cloud. The instructions are preferably executed by computer-executable components preferably integrated with a system and one or more portions of a control module and/or a processor. The computer-readable medium can be stored on any suitable computer readable media such as RAMs, ROMs, flash memory, EEPROMs, optical devices (CD or DVD), hard drives, floppy drives, or any suitable device. The computer-executable component is preferably a general or application specific processor, but any suitable dedicated hardware device or hardware/firmware combination device can additionally or alternatively execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

We claim:
1. A health-monitoring patch system, comprising:
a housing having a user-facing surface;
a microsensor coupled to the housing and having an array of microneedles extending beyond the user-facing surface of the housing to access interstitial fluid in a user's skin, wherein each microneedle forms at least part of one or more electrodes configured to generate one or more electrical signals in response to a presence of an analyte of interest in the interstitial fluid in the user's skin, wherein the one or more electrodes include analyte-detecting regions located at distal ends of the microneedles;
a flexible adhesive substrate including a microsensor opening through which the microsensor extends such that the microneedles are positioned to be inserted within the user's skin, wherein the flexible adhesive substrate surrounds the microsensor and is configured to attach the housing to the user's skin to hold the analyte-detecting regions within the user's skin at a depth less than 350 microns and spaced apart from a surface of the user's skin;
an electronics subsystem positioned within the housing and operably coupled to the microsensor, the electronics subsystem including a microprocessor and an interface, wherein the electronics subsystem is programmed to perform actions including:
receiving the one or more electrical signals from the microsensor, processing the received one or more electrical signals, and wirelessly transmitting, via the interface, the processed signals; and a computing device configured to receive the processed signals and cause information related to the processed signals to be displayed to the user.

2. The system of claim 1 wherein the array of microneedles includes:

a first subarray of the microneedles configured as a first working electrode;

a second subarray of the microneedles configured as a second working electrode;

a third subarray of the microneedles configured as a reference electrode; and a fourth subarray of the microneedles configured as a counter electrode, wherein the one or more electrical signals are dependent on signals received from the first working electrode, the second working electrode, the reference electrode, and the counter electrode.

3. The system of claim 1 wherein one or more microneedles in the array of microneedles include:

a substrate core having a base region connected to a base substrate for the array of microneedles and a tip region opposite the base region;

at least one conductive layer on the tip region of the substrate core; and an insulating layer configured to isolate one or more regions of the at least one conductive layer.

4. The system of claim 3 wherein each of the analyte-detecting regions include:

a sensing layer formed over the insulating layer and configured to enable transduction of a concentration of the analyte of interest to an electrical signal; and a selective coating formed over the sensing layer and having a distribution of molecules that respond to the presence of the analyte of interest.

5. The system of claim 1 wherein one or more microneedles in the array of microneedles is configured to sense a presence of two or more analytes of interest.

6. The system of claim 1 wherein the computing device is a portable electronic device associated with the user, and wherein the electronic device is programmed to receive the processed signals and determine a parameter indicative of at least one health condition of the user based on the processed signals.

7. The system of claim 6 wherein the parameter includes at least one of a temporal trend in an analyte parameter, absolute values of a metric, changes in value of a metric, absolute values of an analyte parameter, or changes in value of an analyte parameter.

8. The system of claim 1 wherein the computing device includes a storage module configured to store a user-specific model to analyze the information received from the interface.

9. The system of claim 1 wherein the computing device includes a software module configured to predict a concentration of the analyte of interest over a period in the future.

10. The system of claim 1 wherein the computing device includes a notification module configured to provide a notification to the user, wherein the notification is based on an analysis of the processed signals received from the interface.

11. The system of claim 1 wherein at least one of the one or more electrical signals is an impedance signal, and wherein the electronics subsystem controls operation of the microsensor to increase detection accuracy based on the impedance signal.

12. The system of claim 11 wherein the electronics subsystem is programmed to detect whether the microsensor is operably coupled to the user for continuous monitoring based on the impedance signal.

13. The system of claim 1, wherein the actions further include a calibration routine.

14. The system of claim 13 wherein the calibration routine includes normalizing signals relative to a grounded portion of the microsensor.

15. The system of claim 1 wherein the computing device is programmed to wirelessly communicate information related to the processed signals to a cloud computing system.

16. A continuous health-monitoring patch system, comprising:

a protective housing;

a flexible adhesive layer coupled to the housing and defining a microsensor opening, the flexible adhesive layer configured to couple to a surface of a user's skin;

a tissue-penetrating microsensor at least partially within the housing and extending through the microsensor opening in the flexible adhesive layer, the tissue-penetrating microsensor configured to access interstitial fluid within the user's skin, wherein the tissue-penetrating microsensor includes:

a first portion forming a first electrode; and a second portion forming a second electrode, wherein the tissue-penetrating microsensor is configured to generate a signal in response to a presence of one or more analytes of interest in the interstitial fluid at least whole the first or second electrodes are positioned within the user's skin and are spaced apart from the surface of the user's skin;

a non-invasive sensor configured to generate output indicative of a state of the user;

an electronics subsystem in communication with the tissue-penetrating microsensor and the non-invasive sensor, the electronics subsystem including a communication component, a microprocessor, and a computer-readable medium containing program instructions that cause the microprocessor to:

receive the output from the non-invasive sensor;

control, based at least in part on the received output from the non-invasive sensor, operation of the first electrode or the second electrode for detecting the presence of the one or more analytes of interest within the user's skin, to compensate for the state of the user;

receive the signal from the tissue-penetrating microsensor controlled base at least in part of the received output;

process the received signal to generate information based on the received signal; and wirelessly communicate, through the communication component, the information generated from the received signal; and a processing subsystem in wireless communication with the electronics subsystem to receive and analyze the information from the electronics subsystem.

17. The system of claim 16 wherein the processing subsystem is implemented in a cloud computing system that includes a data storage unit in communication with the electronics subsystem and configured to receive and store the information for use by the processing subsystem.

18. The system of claim 16 wherein the electronics subsystem is configured to transmit the information to the processing subsystem continuously.

19. The system of claim 16 wherein the electronics subsystem is configured to transmit the information to the processing subsystem in response to a detected connection.

20. The system of claim 16 wherein the processing subsystem includes a notification module configured to provide a notification to an electronic device associated with the user, the notification based on the analysis of the information received from the electronics subsystem.

21. The system of claim 20 wherein the notification includes a directive for the user to perform an action that includes one or more of eating, exercising, and/or resting an amount the processing subsystem determines necessary to affect a body chemistry of the user.

22. The system of claim 16 wherein the tissue-penetrating microsensor includes an array of microneedles positioned to extend through the microsensor opening in the flexible adhesive layer and penetrate the surface of the user's skin.

23. The system of claim 22 wherein the flexible adhesive layer is configured to hold distal ends of the microneedles within the user's skin at a depth less than 350 microns and spaced apart from the surface of the user's skin.

24. The system of claim 22 wherein the first portion of the tissue-penetrating microsensor includes a first subarray of microneedles forming the first electrode, and wherein the second portion of the tissue-penetrating microsensor includes a second subarray of microneedles forming the second electrode.

25. The system of claim 24 wherein microneedles of the first subarray or of the second subarray include analyte-sensing regions at distal ends of the microneedles.

26. The system of claim 22 wherein the tissue-penetrating microsensor further includes a base substrate carrying the array of microneedles, and wherein at least one microneedle in the array of microneedles includes:
   a substrate core having a base region connected to the base substrate and a tip region opposite the base region;
   at least one conductive layer formed on the tip region of the substrate core and configured to transmit the signal in response to the presence of the one or more analytes of interest; and
   an insulating layer formed over the at least one conductive layer and configured to isolate one or more regions of the at least one conductive layer for detecting the presence of the one or more analytes of interest.

27. The system of claim 26 wherein a microneedle of the at least one microneedle further includes an analyte-detecting region at a distal end of the microneedle, and wherein the analyte-detecting region includes:
   a sensing layer formed over the insulating layer and configured to enable transduction of a concentration of the one or more analytes of interest to the signal; and
   a selective coating formed over the sensing layer and having a distribution of molecules that respond to the presence of the one or more analytes of interest.

28. The system of claim 16 wherein the electronics subsystem is configured to periodically send the information for a monitoring period of multiple days.

29. A wearable patch system, comprising:
   a housing;
   a microsensor coupled to the housing and having an array of microneedles, wherein one or more subarrays of microneedles of the array of microneedles form at least part of one or more electrodes configured to generate one or more electrical signals in response to a presence of an analyte of interest in interstitial fluid within a user's skin, wherein the one or more electrodes include analyte-detecting regions located at distal ends of the microneedles of the subarrays;
   an adhesive substrate including a microsensor opening through which the microsensor extends such that the microneedles of the array are positioned to be inserted within the user's skin, wherein the adhesive substrate surrounds the microsensor and is configured (a) to attach the housing to a surface of the user's skin and (b) to hold the analyte-detecting regions within the user's skin and spaced apart from the surface of the user's skin;
   an electronics subsystem positioned within the housing and operably coupled to the microsensor, wherein the electronics subsystem is programmed to perform actions including:
      processing the one or more electrical signals received from the microsensor, and
      wirelessly transmitting the processed signals to a computing device configured to cause information related to the processed signals to be displayed to the user.

* * * * *